United States Patent
Conley et al.

(10) Patent No.: US 9,138,289 B2
(45) Date of Patent: Sep. 22, 2015

(54) ELECTRODE SHEATH FOR ELECTROSURGICAL DEVICE

(75) Inventors: Brian M. Conley, South Berwick, ME (US); Roger D. Greeley, Portsmouth, NH (US); Christopher W. Maurer, Wakefield, MA (US); Anthony R. DePasqua, Newburyport, MA (US)

(73) Assignee: MEDTRONIC ADVANCED ENERGY LLC, Minneapolis, MN (US)

( * ) Notice: Subject to any disclaimer, the term of this patent is extended or adjusted under 35 U.S.C. 154(b) by 864 days.

(21) Appl. No.: 12/824,921

(22) Filed: Jun. 28, 2010

(65) Prior Publication Data

US 2011/0319889 A1    Dec. 29, 2011

(51) Int. Cl.
*A61B 18/14* (2006.01)
*A61B 18/00* (2006.01)

(52) U.S. Cl.
CPC ......... *A61B 18/1482* (2013.01); *A61B 18/1402* (2013.01); *A61B 2018/00029* (2013.01); *A61B 2018/00744* (2013.01); *A61B 2018/00779* (2013.01); *A61B 2218/002* (2013.01)

(58) Field of Classification Search
USPC ............................................. 606/41, 45–50
See application file for complete search history.

(56) References Cited

U.S. PATENT DOCUMENTS

| 2,888,928 | A |   | 6/1959 | Seiger |
| 3,682,130 | A |   | 8/1972 | Jeffers |
| 3,750,650 | A |   | 8/1973 | Ruttgers |
| 3,858,586 | A | * | 1/1975 | Lessen ........................... 606/49 |
| 3,907,339 | A |   | 9/1975 | Stumpf et al. |
| 3,910,277 | A |   | 10/1975 | Zimmer |
| 3,913,581 | A |   | 10/1975 | Ritson et al. |
| 3,924,628 | A |   | 12/1975 | Droegemueller et al. |
| 4,016,881 | A | * | 4/1977 | Rioux et al. ..................... 606/51 |
| 4,018,227 | A |   | 4/1977 | Wallach |
| 4,022,215 | A |   | 5/1977 | Benson |
| 4,060,088 | A |   | 11/1977 | Morrison, Jr. et al. |
| 4,061,135 | A |   | 12/1977 | Widran et al. |
| 4,063,560 | A |   | 12/1977 | Thomas et al. |
| 4,072,152 | A |   | 2/1978 | Linehan |
| 4,082,096 | A |   | 4/1978 | Benson |
| 4,207,897 | A |   | 6/1980 | Lloyd et al. |
| 4,244,371 | A |   | 1/1981 | Farin |
| 4,248,224 | A |   | 2/1981 | Jones |
| 4,275,734 | A |   | 6/1981 | Mitchiner |
| 4,276,874 | A |   | 7/1981 | Wolvek et al. |
| 4,278,090 | A |   | 7/1981 | van Gerven |
| 4,321,931 | A |   | 3/1982 | Hon |
| 4,342,218 | A |   | 8/1982 | Fox |

(Continued)

FOREIGN PATENT DOCUMENTS

WO    2011/088387    7/2011

OTHER PUBLICATIONS

International Search Report and the Written Opinion of the International Searching Authority, Application No. PCT/US2011/042017, dated Aug. 24, 2011, 11 pages.

*Primary Examiner* — Michael Peffley
(74) *Attorney, Agent, or Firm* — Jeffrey J. Hohenshell

(57) ABSTRACT

This invention provides an electrosurgical device comprising a handle, a shaft member distal to the handle, a first electrode tip and a second electrode tip at a distal end of the shaft member with the first electrode tip laterally spaced from the second electrode tip, and an electrode sheath movable to cover and uncover a side of the electrode tips while a distal end of the electrode tips is uncovered to treat tissue.

20 Claims, 18 Drawing Sheets

(56) References Cited

U.S. PATENT DOCUMENTS

| | | |
|---|---|---|
| 4,355,642 A | 10/1982 | Alferness |
| 4,377,168 A | 3/1983 | Rzasa et al. |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,671,274 A | 6/1987 | Scrochenko |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,919,129 A | 4/1990 | Weber et al. |
| 4,931,047 A | 6/1990 | Broadwin et al. |
| 4,932,952 A | 6/1990 | Wojciechowicz, Jr. |
| 4,936,281 A | 6/1990 | Stasz |
| 4,943,290 A | 7/1990 | Rexroth et al. |
| 4,946,460 A | 8/1990 | Merry et al. |
| 4,950,232 A | 8/1990 | Ruzicka et al. |
| 4,985,030 A | 1/1991 | Melzer et al. |
| 4,998,933 A | 3/1991 | Eggers et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelna |
| 5,100,388 A | 3/1992 | Behl et al. |
| 5,108,390 A | 4/1992 | Potocky et al. |
| 5,147,355 A | 9/1992 | Friedman et al. |
| 5,178,133 A | 1/1993 | Pena |
| 5,190,541 A | 3/1993 | Abele et al. |
| 5,195,959 A | 3/1993 | Smith |
| 5,197,963 A * | 3/1993 | Parins .............................. 606/46 |
| 5,197,964 A | 3/1993 | Parins |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,234,428 A | 8/1993 | Kaufman |
| 5,254,116 A | 10/1993 | Baust et al. |
| 5,254,117 A | 10/1993 | Rigby et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,330,521 A | 7/1994 | Cohen |
| 5,334,181 A | 8/1994 | Rubinsky et al. |
| 5,334,193 A | 8/1994 | Nardella |
| 5,336,220 A | 8/1994 | Ryan et al. |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,383,874 A | 1/1995 | Jackson et al. |
| 5,385,148 A | 1/1995 | Lesh et al. |
| 5,395,312 A | 3/1995 | Desai |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,401,272 A | 3/1995 | Perkins |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,417,709 A | 5/1995 | Slater |
| 5,423,807 A | 6/1995 | Mlilder |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,503 A | 8/1995 | Considine et al. |
| 5,443,463 A | 8/1995 | Stern et al. |
| 5,443,470 A | 8/1995 | Stern et al. |
| 5,445,638 A | 8/1995 | Rydell et al. |
| 5,450,843 A | 9/1995 | Moll et al. |
| 5,452,582 A | 9/1995 | Longsworth |
| 5,452,733 A | 9/1995 | Sterman et al. |
| 5,460,629 A | 10/1995 | Shlain et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,490,819 A | 2/1996 | Nicholas et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,562 A | 7/1996 | Giter |
| 5,542,945 A | 8/1996 | Fritzsch |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,556,397 A | 9/1996 | Long et al. |
| 5,558,671 A | 9/1996 | Yates |
| 5,560,362 A | 10/1996 | Sliwa, Jr. et al. |
| 5,562,702 A | 10/1996 | Huitema et al. |
| 5,569,241 A | 10/1996 | Edwards |
| 5,569,243 A | 10/1996 | Kortenbach et al. |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,599,346 A | 2/1997 | Edwards et al. |
| 5,605,539 A | 2/1997 | Buelna et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,647,869 A | 7/1997 | Goble et al. |
| 5,656,029 A | 8/1997 | Imran et al. |
| 5,658,278 A | 8/1997 | Imran et al. |
| 5,671,747 A | 9/1997 | Connor |

(56) References Cited

U.S. PATENT DOCUMENTS

| | | | |
|---|---|---|---|
| 5,673,695 A | 10/1997 | McGee et al. | |
| 5,676,662 A | 10/1997 | Fleischhacker et al. | |
| 5,676,692 A | 10/1997 | Sanghvi et al. | |
| 5,676,693 A | 10/1997 | Lafontaine | |
| 5,678,550 A | 10/1997 | Bassen et al. | |
| 5,680,860 A | 10/1997 | Imran | |
| 5,681,278 A | 10/1997 | Igo et al. | |
| 5,681,294 A | 10/1997 | Osborne et al. | |
| 5,681,308 A | 10/1997 | Edwards et al. | |
| 5,687,723 A | 11/1997 | Avitall | |
| 5,687,737 A | 11/1997 | Branham et al. | |
| 5,688,267 A | 11/1997 | Panescu et al. | |
| 5,690,611 A | 11/1997 | Swartz et al. | |
| 5,697,536 A | 12/1997 | Eggers et al. | |
| 5,697,882 A | 12/1997 | Eggers et al. | |
| 5,697,925 A | 12/1997 | Taylor | |
| 5,697,927 A | 12/1997 | Imran et al. | |
| 5,697,928 A | 12/1997 | Walcott et al. | |
| 5,713,942 A | 2/1998 | Stern | |
| 5,716,389 A | 2/1998 | Walinsky et al. | |
| 5,718,241 A | 2/1998 | Ben-Haim et al. | |
| 5,718,701 A | 2/1998 | Shai et al. | |
| 5,720,775 A | 2/1998 | Lanard | |
| 5,722,402 A | 3/1998 | Swanson et al. | |
| 5,730,074 A | 3/1998 | Peter | |
| 5,730,127 A | 3/1998 | Avitall | |
| 5,730,704 A | 3/1998 | Avitall | |
| 5,733,280 A | 3/1998 | Avitall | |
| 5,735,280 A | 4/1998 | Sherman et al. | |
| 5,735,290 A | 4/1998 | Sterman et al. | |
| 5,743,903 A | 4/1998 | Stern et al. | |
| 5,755,760 A | 5/1998 | Maguire et al. | |
| 5,766,167 A | 6/1998 | Eggers et al. | |
| 5,769,846 A | 6/1998 | Edwards et al. | |
| 5,782,828 A | 7/1998 | Chen et al. | |
| 5,785,706 A | 7/1998 | Bednarek | |
| 5,788,636 A | 8/1998 | Curley | |
| 5,792,140 A | 8/1998 | Tu et al. | |
| 5,797,905 A | 8/1998 | Fleischman et al. | |
| 5,797,960 A | 8/1998 | Stevens et al. | |
| 5,800,428 A | 9/1998 | Nelson et al. | |
| 5,800,482 A | 9/1998 | Pomeranz et al. | |
| 5,810,764 A | 9/1998 | Eggers et al. | |
| 5,810,802 A | 9/1998 | Panescu et al. | |
| 5,827,216 A | 10/1998 | Igo et al. | |
| 5,836,947 A | 11/1998 | Fleischman et al. | |
| 5,840,030 A | 11/1998 | Ferek-Petric et al. | |
| 5,843,021 A | 12/1998 | Edwards et al. | |
| 5,843,152 A | 12/1998 | Tu et al. | |
| 5,844,349 A | 12/1998 | Oakley et al. | |
| 5,846,187 A | 12/1998 | Wells et al. | |
| 5,846,191 A | 12/1998 | Wells et al. | |
| 5,849,028 A | 12/1998 | Chen | |
| 5,861,021 A | 1/1999 | Thome et al. | |
| 5,871,523 A | 2/1999 | Fleischman et al. | |
| 5,871,525 A | 2/1999 | Edwards et al. | |
| 5,873,845 A | 2/1999 | Cline et al. | |
| 5,873,855 A | 2/1999 | Eggers et al. | |
| 5,876,399 A | 3/1999 | Chia et al. | |
| 5,879,295 A | 3/1999 | Li et al. | |
| 5,879,296 A | 3/1999 | Ockuly et al. | |
| 5,879,348 A | 3/1999 | Owens et al. | |
| 5,881,732 A | 3/1999 | Sung et al. | |
| 5,882,346 A | 3/1999 | Pomeranz et al. | |
| 5,885,278 A | 3/1999 | Fleischman | |
| 5,891,142 A | 4/1999 | Eggers et al. | |
| 5,893,848 A | 4/1999 | Negus et al. | |
| 5,895,355 A | 4/1999 | Schaer | |
| 5,895,417 A | 4/1999 | Pomeranz et al. | |
| 5,897,553 A | 4/1999 | Mulier | |
| 5,897,554 A | 4/1999 | Chia et al. | |
| 5,899,898 A | 5/1999 | Arless et al. | |
| 5,899,899 A | 5/1999 | Arless et al. | |
| 5,902,289 A | 5/1999 | Swartz et al. | |
| 5,904,711 A | 5/1999 | Flom et al. | |
| 5,906,580 A | 5/1999 | Kline-Schoder et al. | |
| 5,906,587 A | 5/1999 | Zimmon | |
| 5,906,606 A | 5/1999 | Chee et al. | |
| 5,908,029 A | 6/1999 | Knudson et al. | |
| 5,913,854 A | 6/1999 | Maguire et al. | |
| 5,916,213 A | 6/1999 | Haissaguerre et al. | |
| 5,916,214 A | 6/1999 | Cosio et al. | |
| 5,921,924 A | 7/1999 | Avitall | |
| 5,921,982 A | 7/1999 | Lesh et al. | |
| 5,925,045 A | 7/1999 | Reimels et al. | |
| 5,927,284 A | 7/1999 | Borst et al. | |
| 5,928,191 A | 7/1999 | Houser et al. | |
| 5,931,810 A | 8/1999 | Grabek | |
| 5,931,848 A | 8/1999 | Saadat | |
| 5,935,123 A | 8/1999 | Edwards et al. | |
| 5,944,715 A | 8/1999 | Goble et al. | |
| 5,954,661 A | 9/1999 | Greenspon et al. | |
| 5,957,919 A | 9/1999 | Laufer | |
| 5,971,980 A | 10/1999 | Sherman | |
| 5,971,983 A | 10/1999 | Lesh | |
| 5,980,516 A | 11/1999 | Mulier et al. | |
| 5,989,248 A | 11/1999 | Tu et al. | |
| 5,993,412 A | 11/1999 | Deily et al. | |
| 5,993,447 A | 11/1999 | Blewett et al. | |
| 6,004,316 A | 12/1999 | Laufer | |
| 6,004,319 A | 12/1999 | Goble et al. | |
| 6,007,499 A | 12/1999 | Martin et al. | |
| 6,010,500 A | 1/2000 | Sherman et al. | |
| 6,012,457 A | 1/2000 | Lesh | |
| 6,015,391 A | 1/2000 | Rishton et al. | |
| 6,016,811 A | 1/2000 | Knopp et al. | |
| 6,018,676 A | 1/2000 | Davis et al. | |
| 6,019,757 A | 2/2000 | Scheldrup | |
| 6,024,733 A | 2/2000 | Eggers et al. | |
| 6,030,381 A | 2/2000 | Jones et al. | |
| 6,036,687 A | 3/2000 | Laufer et al. | |
| 6,042,556 A | 3/2000 | Beach et al. | |
| 6,048,333 A | 4/2000 | Lennox et al. | |
| 6,056,744 A | 5/2000 | Edwards | |
| 6,056,745 A | 5/2000 | Panescu et al. | |
| 6,056,746 A | 5/2000 | Goble | |
| 6,056,747 A | 5/2000 | Saadat et al. | |
| 6,063,081 A | 5/2000 | Mulier | |
| 6,066,139 A | 5/2000 | Ryan et al. | |
| 6,068,653 A | 5/2000 | LaFontaine | |
| 6,071,279 A | 6/2000 | Whayne et al. | |
| 6,083,237 A | 7/2000 | Huitema et al. | |
| 6,086,585 A | 7/2000 | Hovda et al. | |
| 6,088,894 A | 7/2000 | Oakley | |
| 6,096,037 A | 8/2000 | Mulier | |
| 6,113,592 A | 9/2000 | Taylor | |
| 6,113,596 A | 9/2000 | Hooven et al. | |
| 6,117,101 A | 9/2000 | Diederich et al. | |
| 6,120,496 A | 9/2000 | Whayne et al. | |
| 6,141,576 A | 10/2000 | Littmann et al. | |
| 6,142,993 A | 11/2000 | Whayne et al. | |
| 6,142,994 A | 11/2000 | Swanson et al. | |
| 6,149,620 A | 11/2000 | Baker et al. | |
| 6,152,920 A | 11/2000 | Thompson et al. | |
| 6,161,543 A | 12/2000 | Cox et al. | |
| 6,165,172 A * | 12/2000 | Farley et al. | 606/33 |
| 6,165,174 A | 12/2000 | Jacobs et al. | |
| 6,179,832 B1 * | 1/2001 | Jones et al. | 606/32 |
| 6,190,384 B1 | 2/2001 | Ouchi | |
| 6,193,716 B1 | 2/2001 | Shannon, Jr. | |
| 6,210,406 B1 | 4/2001 | Webster | |
| 6,210,410 B1 | 4/2001 | Farin et al. | |
| 6,210,411 B1 | 4/2001 | Hofmann et al. | |
| 6,212,426 B1 | 4/2001 | Swanson | |
| 6,217,528 B1 | 4/2001 | Koblish et al. | |
| 6,217,575 B1 | 4/2001 | DeVore | |
| 6,217,576 B1 | 4/2001 | Tu et al. | |
| 6,224,592 B1 | 5/2001 | Eggers et al. | |
| 6,231,518 B1 | 5/2001 | Grabek et al. | |
| 6,231,591 B1 | 5/2001 | Desai | |
| 6,235,020 B1 | 5/2001 | Cheng et al. | |
| 6,235,024 B1 | 5/2001 | Tu | |
| 6,237,605 B1 | 5/2001 | Vaska et al. | |
| 6,238,347 B1 | 5/2001 | Nix et al. | |

(56) References Cited

U.S. PATENT DOCUMENTS

| | | |
|---|---|---|
| 6,238,387 B1 | 5/2001 | Miller, III |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,110 B1 | 6/2001 | Wampler |
| 6,251,128 B1 | 6/2001 | Knopp et al. |
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,270,471 B1 | 8/2001 | Hechel et al. |
| 6,283,988 B1 | 9/2001 | Laufer et al. |
| 6,283,989 B1 | 9/2001 | Laufer et al. |
| 6,293,943 B1 | 9/2001 | Panescu et al. |
| 6,296,619 B1 | 10/2001 | Brisken et al. |
| 6,299,633 B1 | 10/2001 | Laufer |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carner et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,680 B1 | 12/2002 | Francischelli |
| 6,502,575 B1 | 1/2003 | Jacobs et al. |
| 6,508,815 B1 | 1/2003 | Strul et al. |
| 6,514,250 B1 | 2/2003 | Jahns |
| 6,517,536 B2 | 2/2003 | Hooven et al. |
| 6,527,767 B2 | 3/2003 | Wang et al. |
| 6,537,248 B2 | 3/2003 | Mulier |
| 6,537,272 B2 | 3/2003 | Christopherson et al. |
| 6,558,379 B1 | 5/2003 | Batchelor et al. |
| 6,558,382 B2 | 5/2003 | Jahns |
| 6,558,385 B1 | 5/2003 | McClurken et al. |
| 5,697,536 C1 | 6/2003 | Eggers et al. |
| 6,575,969 B1 | 6/2003 | Rittman, III et al. |
| 6,579,288 B1 | 6/2003 | Swanson et al. |
| 6,584,360 B2 | 6/2003 | Francischelli |
| 6,585,732 B2 | 7/2003 | Mulier |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,663,627 B2 | 12/2003 | Francischelli |
| 6,666,862 B2 | 12/2003 | Jain et al. |
| 6,679,882 B1 | 1/2004 | Kornerup |
| 6,682,501 B1 | 1/2004 | Nelson |
| 6,689,131 B2 | 2/2004 | McClurken |
| 6,692,450 B1 | 2/2004 | Coleman |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,766,202 B2 | 7/2004 | Underwood et al. |
| 6,766,817 B2 | 7/2004 | da Silva |
| 6,773,433 B2 | 8/2004 | Stewart et al. |
| 6,775,575 B2 | 8/2004 | Bommannan et al. |
| 6,776,780 B2 | 8/2004 | Mulier |
| 6,780,180 B1 * | 8/2004 | Goble et al. .................. 606/41 |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | McClurken et al. |
| 6,960,205 B2 | 11/2005 | Jahns |
| 6,962,589 B2 | 11/2005 | Mulier |
| 7,066,586 B2 | 6/2006 | da Silva |
| 7,115,139 B2 | 10/2006 | McClurken et al. |
| 7,156,845 B2 | 1/2007 | Mulier et al. |
| 7,166,106 B2 | 1/2007 | Bartel et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,537,595 B2 | 5/2009 | McClurken |
| 7,604,635 B2 | 10/2009 | McClurken et al. |
| 7,645,277 B2 | 1/2010 | McClurken et al. |
| 7,651,494 B2 | 1/2010 | McClurken et al. |
| 7,736,361 B2 | 6/2010 | Palanker |
| 7,815,634 B2 | 10/2010 | McClurken et al. |
| 7,909,820 B2 | 3/2011 | Lipson |
| 7,976,544 B2 | 7/2011 | McClurken et al. |
| 7,998,140 B2 | 8/2011 | McClurken |
| 8,012,154 B2 | 9/2011 | Livneh |
| 8,038,670 B2 | 10/2011 | McClurken |
| 8,083,736 B2 | 12/2011 | McClurken et al. |
| 8,177,783 B2 | 5/2012 | Davison et al. |
| 8,216,233 B2 | 7/2012 | McClurken et al. |
| 8,323,276 B2 | 12/2012 | Palanker et al. |
| 8,348,946 B2 | 1/2013 | McClurken et al. |
| 8,361,068 B2 | 1/2013 | McClurken |
| 8,475,455 B2 | 7/2013 | McClurken et al. |

(56) References Cited

U.S. PATENT DOCUMENTS

| | | |
|---|---|---|
| 8,568,409 B2 | 10/2013 | O'Brien et al. |
| 8,632,533 B2 | 1/2014 | Greeley et al. |
| 8,882,756 B2 | 11/2014 | Greeley et al. |
| 8,906,012 B2 | 12/2014 | Conley et al. |
| 8,920,417 B2 | 12/2014 | Conley et al. |
| 8,979,842 B2 | 3/2015 | McNall, III et al. |
| 2001/0051802 A1 | 12/2001 | Woloszko et al. |
| 2002/0049483 A1 | 4/2002 | Knowlton |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2005/0267467 A1 | 12/2005 | Paul et al. |
| 2006/0009756 A1 | 1/2006 | Francischelli |
| 2006/0009759 A1 | 1/2006 | Christian |
| 2006/0064085 A1 | 3/2006 | Schechter et al. |
| 2007/0049920 A1 | 3/2007 | McClurken et al. |
| 2007/0093808 A1 | 4/2007 | Mulier et al. |
| 2007/0112343 A1 | 5/2007 | Mische et al. |
| 2007/0118114 A1 | 5/2007 | Miller et al. |
| 2007/0208332 A1 | 9/2007 | Mulier et al. |
| 2008/0015563 A1 | 1/2008 | Hoey et al. |
| 2008/0021450 A1 | 1/2008 | Couture |
| 2008/0058796 A1 | 3/2008 | O'Brien et al. |
| 2008/0071270 A1 | 3/2008 | Desinger et al. |
| 2008/0103494 A1 | 5/2008 | Rioux |
| 2008/0234674 A1 | 9/2008 | McClurken et al. |
| 2009/0209975 A1 | 8/2009 | Milijasevic et al. |
| 2009/0222001 A1 | 9/2009 | Greeley et al. |
| 2009/0264879 A1 | 10/2009 | McClurken et al. |
| 2010/0100095 A1 | 4/2010 | McClurken et al. |
| 2011/0028965 A1 | 2/2011 | McClurken |
| 2012/0004657 A1 | 1/2012 | Conley et al. |
| 2012/0101496 A1 | 4/2012 | McClurken et al. |
| 2012/0116397 A1 | 5/2012 | Rencher et al. |
| 2012/0191084 A1 | 7/2012 | Davison et al. |
| 2014/0188105 A1 | 7/2014 | Conley et al. |

* cited by examiner

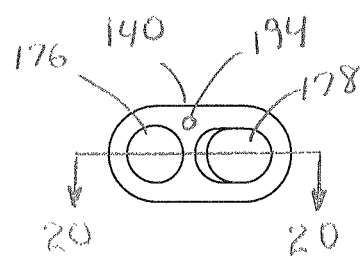
FIG. 19
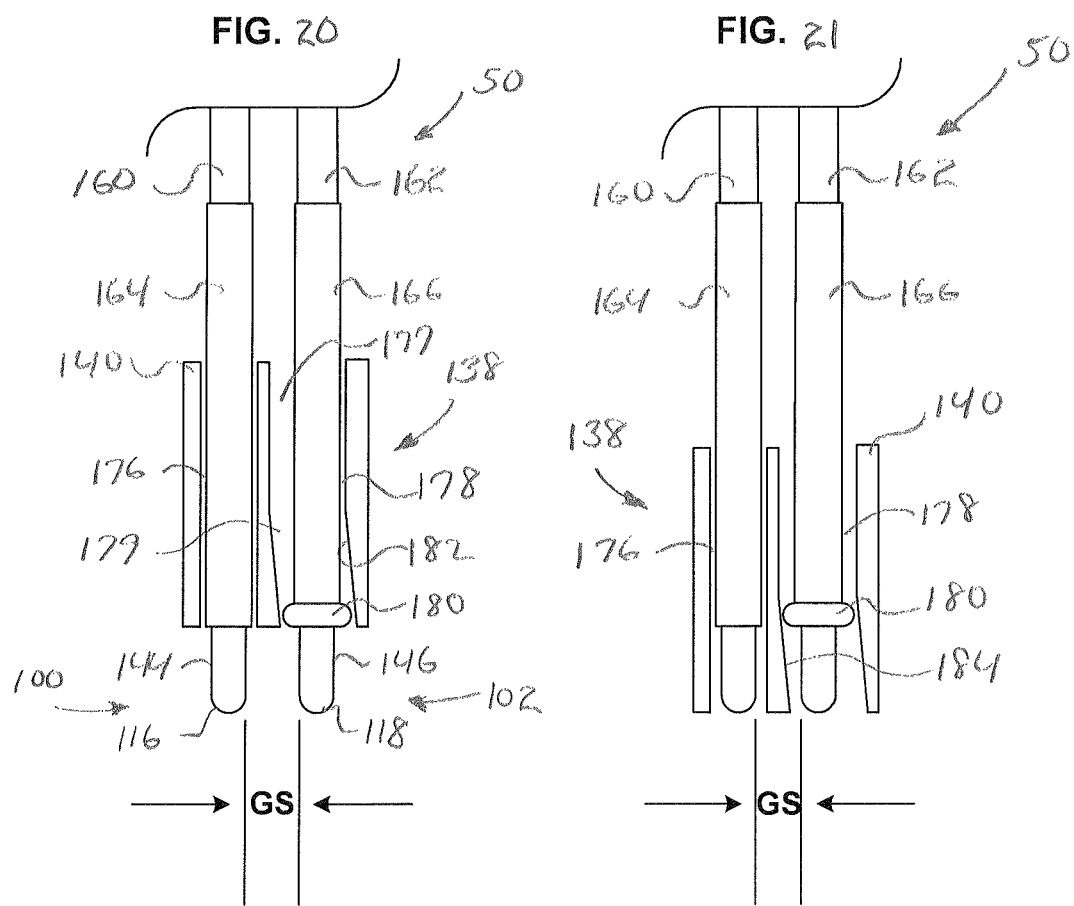
FIG. 20
FIG. 21

ELECTRODE SHEATH FOR ELECTROSURGICAL DEVICE

FIELD

This invention relates generally to the field of medical systems, devices and methods for use upon a human body during surgery. More particularly, the invention relates to electrosurgical systems, devices and methods for use upon tissues of a human body during surgery, particularly open surgery and minimally invasive surgery such as laparoscopic surgery.

BACKGROUND

In certain surgical procedures, a bipolar electrosurgical device may have electrodes with relatively large surface areas which are intended to treat relatively large areas of tissue to expedite treatment thereof. However, also as part of the same surgical procedure, it may be desirable to treat much smaller areas of tissue without treating tissue adjacent to the desired treatment area. In this situation, another bipolar electrosurgical device with smaller electrodes may be used to focus treatment in the smaller treatment area.

In addition, during the foregoing surgical procedure, it may be desirable to have multiple bipolar devices with each providing different spacing between the electrodes to change the treatment of the tissue and/or size of the footprint of the electrodes. For example, a device with the electrodes spaced further apart may provide a deeper depth of tissue treatment and have a larger electrode footprint than a device with the same size electrodes positioned closer together, which may result in a more shallow tissue treatment and a smaller electrode footprint which can better access particularly confined spaces.

What is needed is a bipolar electrosurgical device which may be used to treat relatively large areas of tissue, as well as electrodes which may be effectively decreased in size to focus tissue treatment on a particularly small tissue treatment site/area without treating tissue adjacent to the site area. What is also needed is a bipolar device which can change the relative spacing between the electrodes so the depth of tissue treatment and/or size of the footprint of the electrodes.

SUMMARY OF THE INVENTION

This invention provides a fluid-assisted electrosurgical device to treat tissue in a presence of radio frequency energy and a fluid provided from the device. In one embodiment, the device comprises a handle, a shaft member distal to the handle, a first electrode tip and a second electrode tip distal a distal end of the shaft member with the first electrode tip laterally spaced from the second electrode tip, and an electrode sheath movable to cover and uncover a side of the electrode tips while a distal end of the electrode tips is uncovered or exposed to treat tissue.

In other embodiments, the sheath may include a tubular passage and the shaft member may be within the tubular passage of the sheath so that the sheath overlies the shaft member.

In other embodiments, the sheath may be movable distally to cover the side of the electrode tips, and movable proximally to uncover or expose the side of the electrode tips.

In certain embodiments, the sheath may be operable with the shaft member to limit distal and proximal movement of the sheath. More particularly, the sheath and shaft member may have cooperating elements which limit the distal and proximal movement of the sheath. Even more particularly, the cooperating elements may comprise a protrusion located on the shaft member, and a slot located on the sheath which contains the protrusion.

In other embodiments, the sheath may be operable with the shaft member to increase and decrease a lateral spacing of the electrode tips relative to each other. More particularly, the sheath may be movable distally to cover the side of the electrode tips and decrease the lateral spacing of the electrode tips relative to each other, and movable proximally to uncover and expose the side of the electrode tips and increase the lateral spacing of the electrode tips relative to each other.

In other embodiments, the sheath may be operable with the shaft member to increase and decrease a lateral spacing of the electrode tips relative to each other by moving at least one of the electrode tips and/or a portion of the shaft member.

In other embodiments, the sheath may comprise a first tubular passage and a second tubular passage, and a distal portion of the second tubular passage may be angled relative to the first tubular passage. The sheath may be operable with the shaft member to increase and decrease a lateral spacing of the electrode tips relative to each other by contacting a surface of the sheath defining the angled portion of the second tubular passage with a portion of the shaft member located therein as the sheath is moved proximally and distally, respectfully.

In other embodiments, the sheath may also be operable with at least one of the electrode tips to increase and decrease a lateral spacing of the electrode tips relative to each other by contacting a surface of the sheath defining the angled portion of the second tubular passage with a portion of one of the electrode tips located therein as the sheath is moved proximally and distally, respectfully.

In other embodiments, the sheath may be operable with at least one of the electrode tips to increase and decrease a lateral spacing of the electrode tips relative to each other, particularly by moving at least one of the electrode tips.

In other embodiments, the device may include a sheath actuation mechanism which extends from the handle and connects to the sheath to activate movement of the sheath from the handle. The sheath actuation mechanism may comprise an elongated member which pushes the sheath distally and pulls the sheath proximally.

BRIEF DESCRIPTION OF THE DRAWINGS

FIG. 19 is a top view of the electrode sheath of FIGS. 17 and 18.

FIG. 20 is a cross-sectional view of the electrode sheath of FIGS. 17 and 18 taken along line 20-20 of FIG. 18 with sheath in a retracted position relative to the shaft member;

FIG. 21 is a cross-sectional view of the electrode sheath of FIGS. 17 and 18 taken along line 20-20 of FIG. 18 with sheath in an extended position relative to the shaft member;

DETAILED DESCRIPTION

Figure 1:
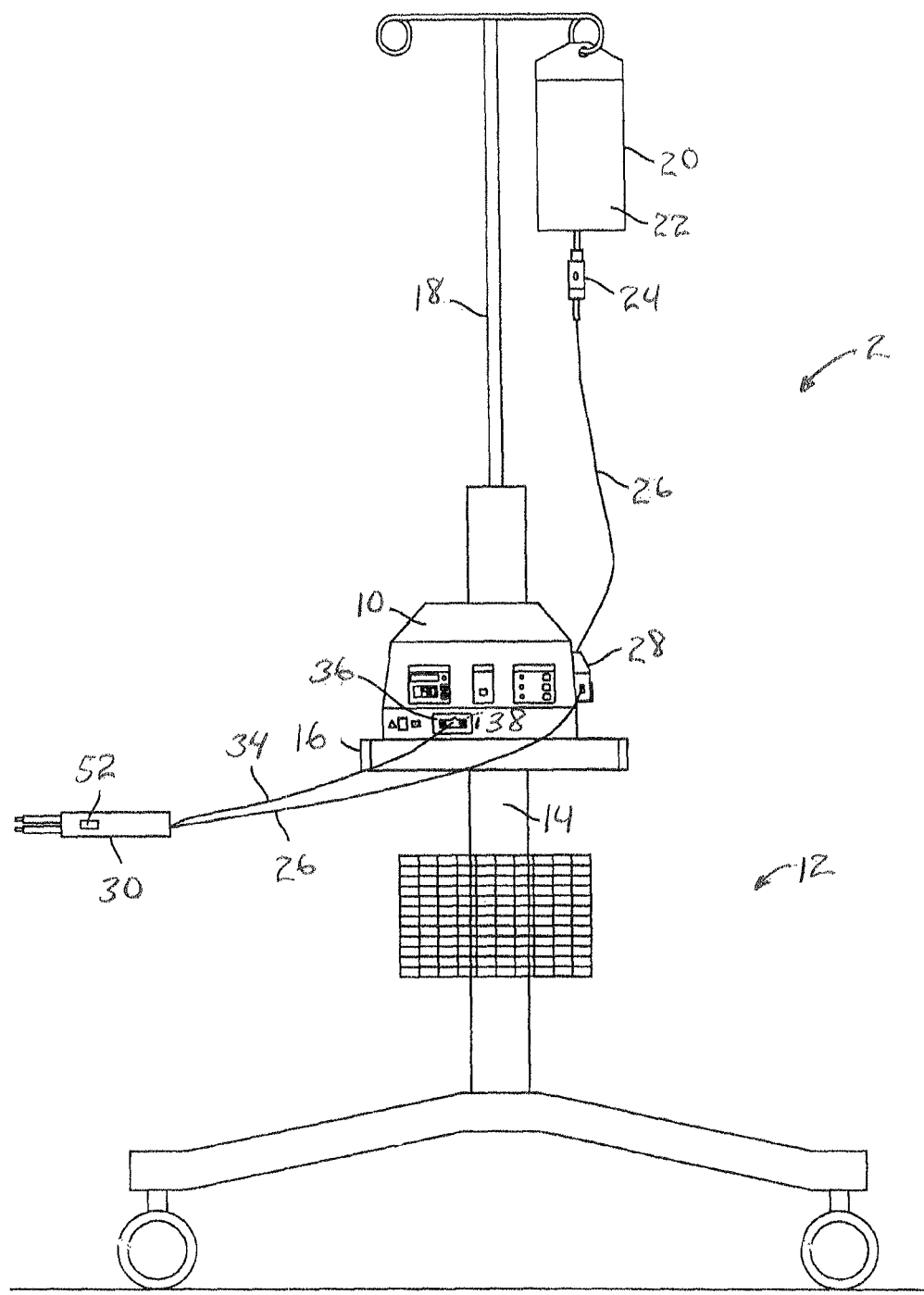
FIG. 1 is a front view of one embodiment of a system of the present invention having an electrosurgical unit in combination with a fluid source and handheld electrosurgical device.

Throughout the description, like reference numerals and letters indicate corresponding structure throughout the several views. Also, any particular feature(s) of a particular exemplary embodiment may be equally applied to any other exemplary embodiment(s) of this specification as suitable. In other words, features between the various exemplary embodiments described herein are interchangeable as suitable, and not exclusive. From the specification, it should be clear that any use of the terms "distal" and "proximal" are made in reference from the user of the device, and not the patient.

The invention provides systems, devices and methods for treating tissue at a tissue treatment site during an electrosurgical procedure. This is particularly useful for procedures where it is desirable to shrink, coagulate and seal tissue against blood loss, for example, by shrinking lumens of blood vessels (e.g., arteries, veins).

The invention will now be discussed with reference to the figures, with FIG. 1 showing a front view of one embodiment of a system 2 of the present invention having an electrosurgical unit 10 in combination with a fluid source 20 and a handheld electrosurgical device 30. FIG. 1 further shows a movable cart 12 having a support member 14 which carries a platform 16 comprising a pedestal table to provide a flat, stable surface for location of the electrosurgical unit 10. As shown cart 2 further comprises a fluid source carrying pole 18 with a cross support for carrying fluid source 20.

As shown in FIG. 1, fluid source 20 comprises a bag of fluid from which a fluid 22 flows through a drip chamber 24 after the bag is penetrated with a spike located at the end of the drip chamber 24. Thereafter, fluid 22 flows through a fluid passage provided by a lumen 27 of flexible, plastic fluid delivery tubing 26 to handheld electrosurgical device 30.

As shown in FIG. 1, the fluid delivery tubing 26 passes through pump 28. Pump 28 comprises a peristaltic pump and, more specifically, a rotary peristaltic pump. With a rotary peristaltic pump, a portion of the fluid delivery tubing 26 is loaded into the pump 28 by raising and lowering a pump head in a known manner. Fluid 22 is then conveyed within the fluid delivery tubing 26 by waves of contraction placed externally on the tubing 26 which are produced mechanically, typically by rotating pinch rollers which rotate on a drive shaft and intermittently compress the fluid delivery tubing 26 against an anvil support. Alternatively, pump 28 may comprise a linear peristaltic pump. With a linear peristaltic pump, fluid 22 is conveyed within the fluid delivery tubing 26 by waves of contraction placed externally on the tubing 26 which are produced mechanically, typically by a series of compression fingers or pads which sequentially squeeze the tubing 26 against a support. Peristaltic pumps are generally preferred, as the electro-mechanical force mechanism, here rollers driven by electric motor, does not make contact with the fluid 22, thus reducing the likelihood of inadvertent contamination.

In one embodiment, the fluid 22 is liquid saline solution, and even more particularly, normal (physiologic) saline solution. However, although the description herein may make reference to saline as the fluid 22, other electrically conductive fluids may be used in accordance with the invention.

In addition to the use of an electrically conductive fluid, as will become more apparent with further reading of this specification, fluid 22 may also be an electrically non-conductive fluid. The use of a non-conductive fluid may not offer as many advantages as a conductive fluid, however, the use of a non-conductive fluid still provides certain advantages over the use of a dry electrode including, for example, reduced occurrence of tissue sticking to the electrode(s) of device 30 and cooling of the electrode(s) and/or tissue. Therefore, it is also within the scope of the invention to include the use of a non-conductive fluid, such as, for example, deionized water.

As shown in FIG. 1, electrosurgical device 30 is connected to electrosurgical unit 10 via a cable 34 which has a plurality of electrically insulated wire conductors 42 (shown in FIG. 5) and at least one plug 36 at the end thereof. The electrosurgical unit 10 provides radio-frequency (RF) energy via cable 34 to electrosurgical device 30. Plug receptacle 38 of electrosurgical unit 10 receives the plug 36 of device 30 therein to electrically connect device 30 to the electrosurgical unit 10. The fluid delivery tubing 26 may be provided as part of cable 34 and produced with the electrically insulated wires 42 via plastic co-extrusion.

Figure 2:
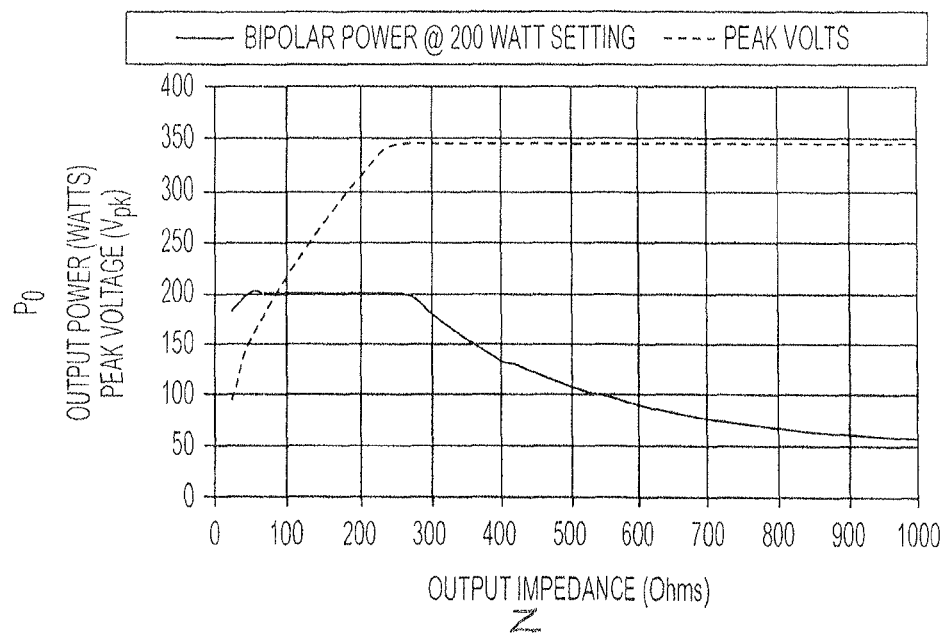
FIG. 2 is a graph of the RF power output versus impedance for the electrosurgical unit of FIG. 1.

An exemplary RF power output curve for electrosurgical unit 10 is shown in FIG. 2. Impedance Z, shown in units of ohms on the X-axis and RF output power $P_O$ is shown in units of watts on the Y-axis. In the illustrated embodiment, the RF power is bipolar and set to 200 watts. As shown in the figure, for an RF power setting $P_S$ of 200 watts, the output power $P_O$ will remain constant with the set RF power $P_S$ as long as the impedance Z stays between the low impedance cut-off of 30 ohms and the high impedance cut-off of 250 ohms. Below an impedance Z of 30 ohms, the output power $P_O$ will decrease as shown by the low impedance ramp. Above an impedance Z of 250 ohms, the output power $P_O$ will also decrease as shown by the high impedance ramp.

Figure 3:
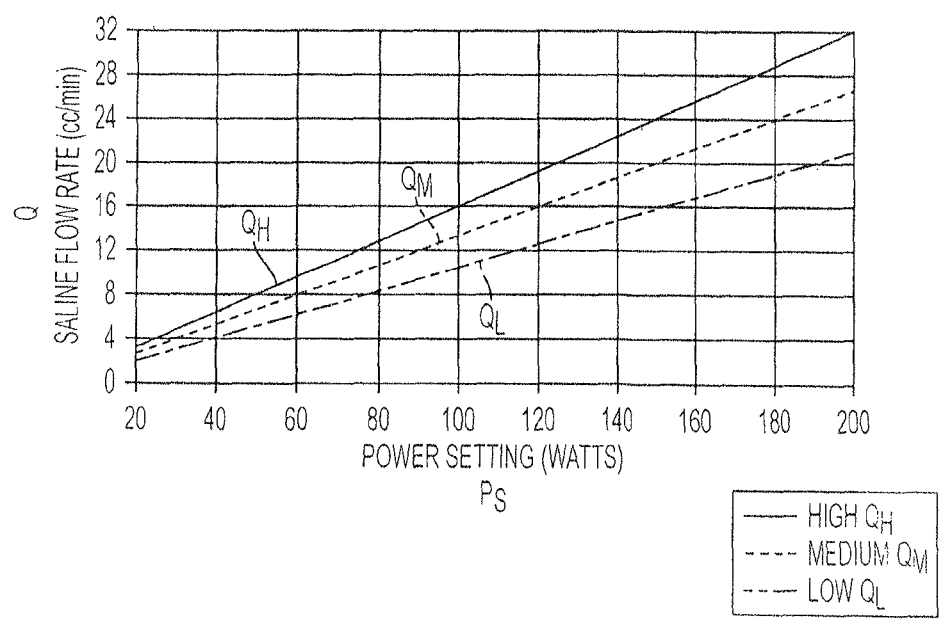
FIG. 3 is graph showing a relationship of fluid flow rate Q in units of cubic centimeters per minute (cc/min) on the Y-axis, and the RF power setting $P_S$ in units of watts on the X-axis.

Electrosurgical unit 10 has also been configured such that the speed of pump 28, and therefore the throughput of fluid 22 expelled by the pump 28, is predetermined based on two input variables, the RF power setting and the fluid flow rate setting. In FIG. 3, there is shown a relationship of fluid flow rate Q in units of cubic centimeters per minute (cc/min) on the Y-axis, and the RF power setting $P_S$ in units of watts on the X-axis. The relationship has been engineered to inhibit undesirable effects such as tissue desiccation, electrode sticking, smoke production and char formation, while at the same time not providing a fluid flow rate Q at a corresponding RF power setting $P_S$ which is so great as to provide too much fluid 22 from device 30, which may result in too much electrical dispersion and excess cooling at the electrode/tissue interface.

As shown, electrosurgical unit 10 has been configured to increase the fluid flow rate Q linearly with an increasing RF power setting $P_S$ for each of three fluid flow rate settings of low, medium and high corresponding to $Q_L$, $Q_M$ and $Q_H$, respectively. Conversely, electrosurgical unit 10 has been configured to decrease the fluid flow rate Q linearly with an decrease RF power setting $P_S$ for each of three fluid flow rate settings of low, medium and high corresponding to $Q_L$, $Q_M$ and $Q_H$, respectively.

Electrosurgical unit 10 may be particularly configured for use with an electrosurgical device 30 which is a bipolar device. With a bipolar device, an alternating current (AC) electrical circuit is created between first and second electrical poles/electrodes of the device 30. An exemplary bipolar electrosurgical device of the present invention which may be used in conjunction with electrosurgical unit 10 of the present invention is shown at reference character 30a in FIG. 4. While electrosurgical device 30a of the present invention is described herein with reference to use with electrosurgical unit 10, it should be understood that the description of the combination is for purposes of illustrating the system of the invention. Consequently, it should be understood that while electrosurgical device 30a disclosed herein may be used with electrosurgical unit 10, it may be plausible to use other electrosurgical devices with electrosurgical unit, or it may be plausible to use the electrosurgical device(s) disclosed herein with another electrosurgical unit.

Figure 4:
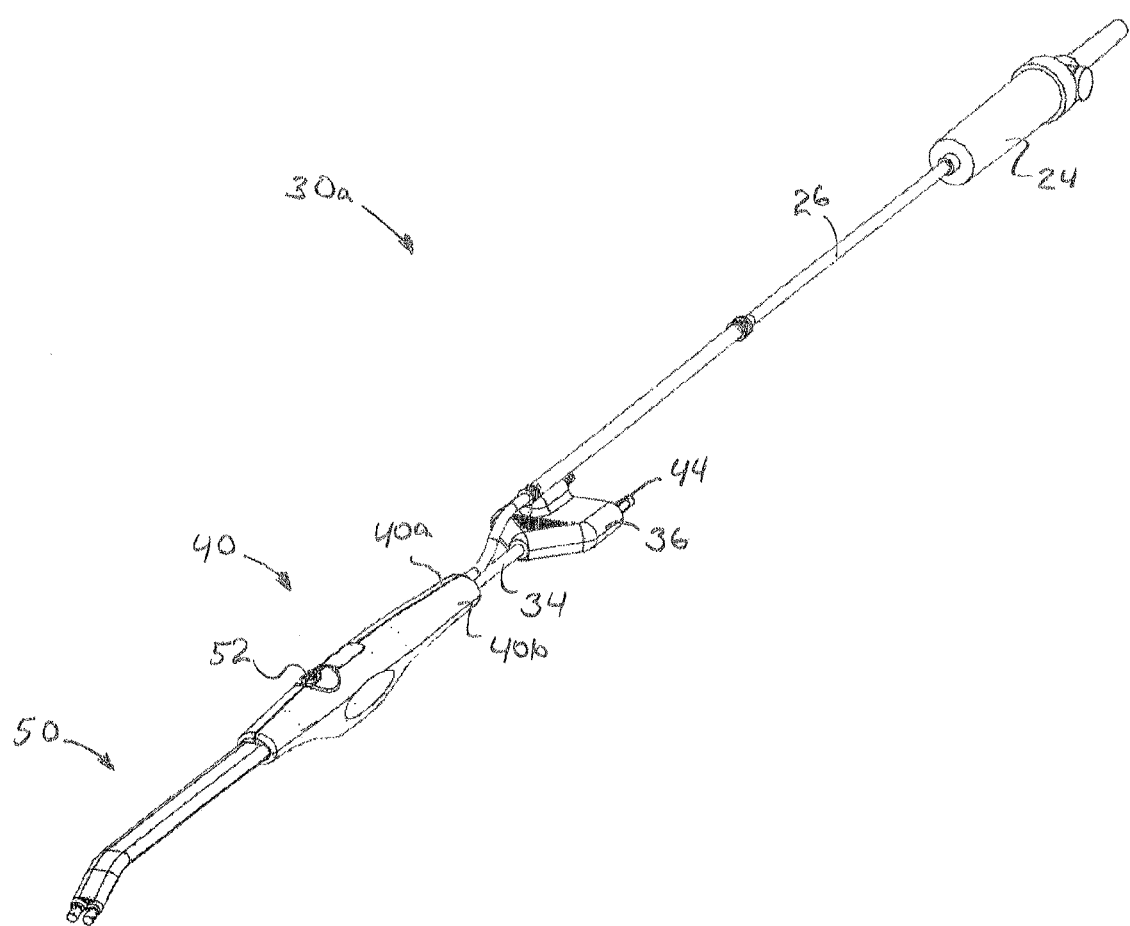
FIG. 4 is a perspective view of an electrosurgical device according to the present invention.

As shown in FIG. 4, exemplary bipolar device 30a comprises a proximal handle 40 comprising mating handle portions 40a, 40b. Handle 40 is particularly made of a sterilizable, rigid, non-conductive material, such as a plastic material (e.g., thermoplastic such as acrylonitrile-butadiene-styrene (ABS), polycarbonate (PC)). Also, handle 40 is particularly configured slender, along with the rest of device 30a, to facilitate a user of device 30a to hold and manipulate device 30a like a pen-type device. Device 30a also includes a cable 34 which is connectable to electrosurgical unit 10 and flexible fluid delivery tubing 26 which is connectable to fluid source 20, particularly via a spike located at the end of drip chamber 24, which respectively provide RF energy and fluid 22 to exposed electrode tips provide by electrodes 100, 102.

Figure 5:
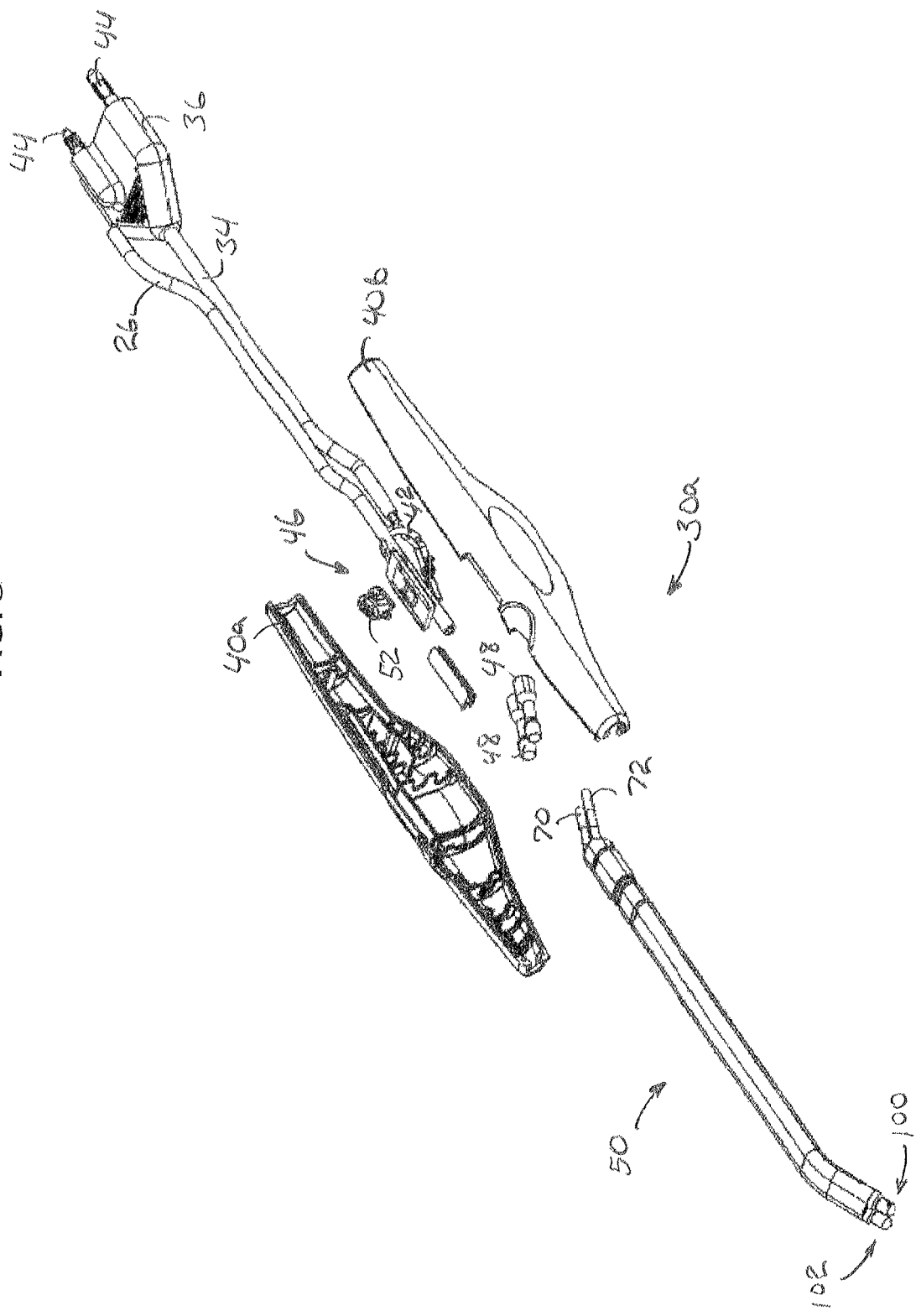
FIG. 5 is an exploded perspective view of the device of FIG. 4.

As shown in FIG. 5, cable 34 of device 30a comprises a plurality of insulated wires 42 connectable to electrosurgical unit 10 via three banana (male) plug connectors 44. The banana plug connectors 44 are each assembled with wire conductors of insulated wires 42 within plug 36 in a known manner. Wire conductors of insulated wires 42 are connected distally to a handswitch assembly 46, and thereafter wire conductors are connected to crimp terminals 48 which connect to a proximal portion of conductors 70, 72 of shaft member 50.

Handswitch assembly 46 comprises a push button 52 which overlies a domed switch. Upon depression of button 52, the domed switch forms a closed circuit which is sensed by electrosurgical unit 10, which then provides RF power to the electrodes 100, 102.

Figure 6:
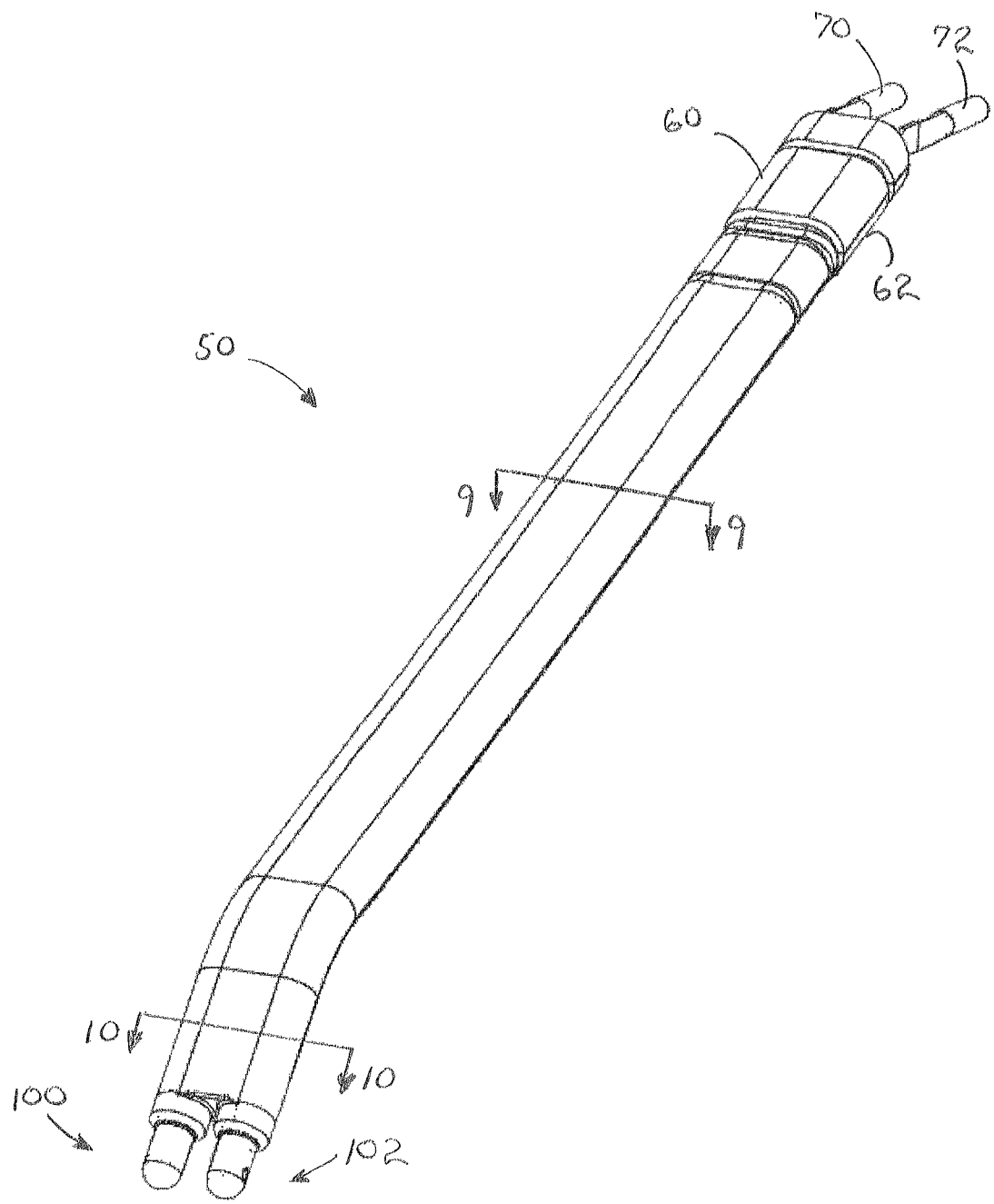
FIG. 6 is a close-up front perspective view of the shaft member of the device of FIG. 4.
Figure 7:
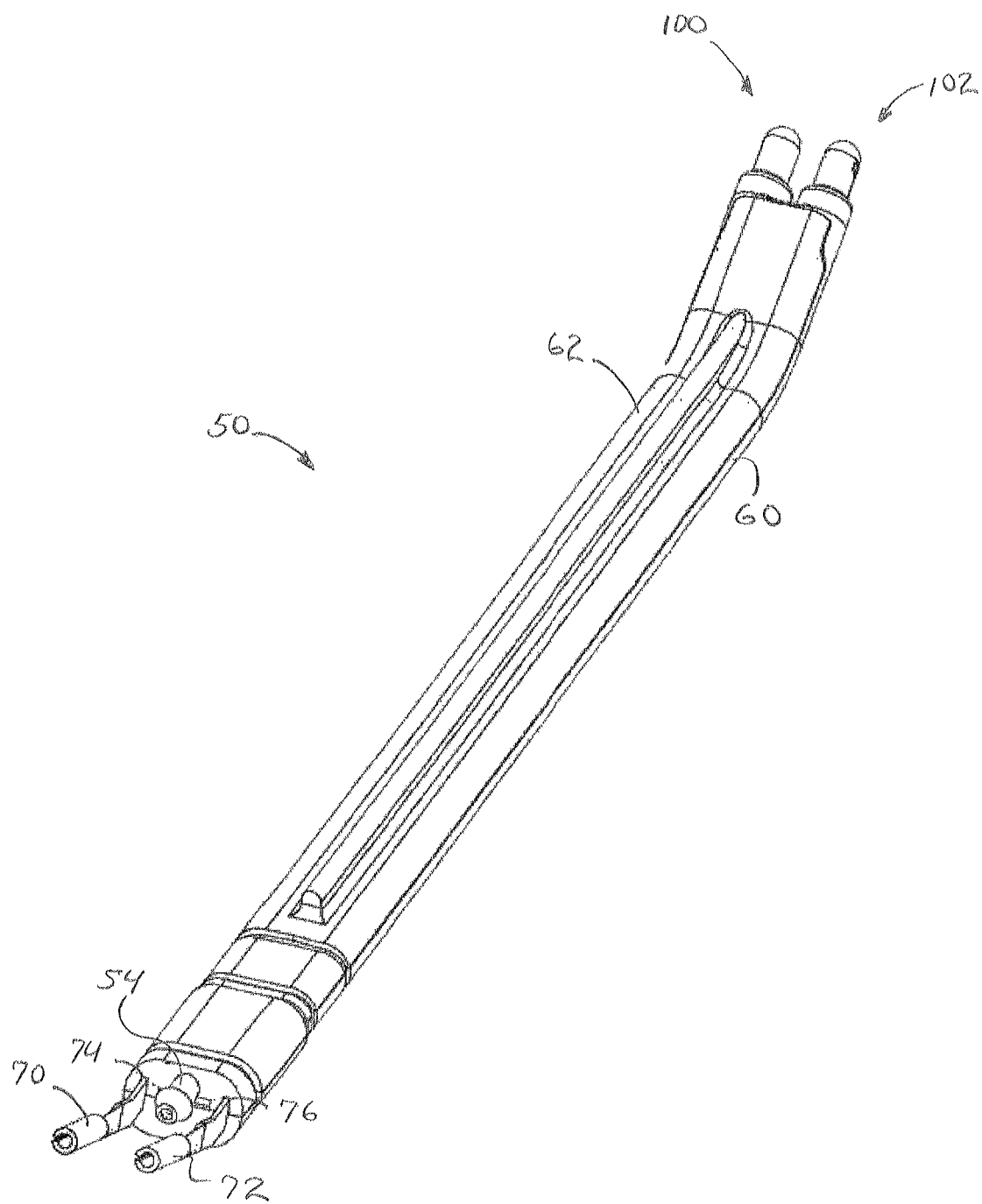
FIG. 7 is a close-up rear perspective view of the shaft member of the device of FIG. 4.

Referring to FIGS. 6 and 7, rigid shaft member 50, located distal to handle 40, comprises a shaft member first body 60 and a shaft member second body 62. Shaft member 50 extends distally from the handle 40 and supports electrodes 100, 102 in rigid relation to the handle 40.

At a proximal end 56 of shaft member 50, fluid delivery tubing 26 of device 30a is connected within handle 40 to a proximal barbed connector portion 54 of shaft member 50, which is defined by at least one of shaft member first body 60 and shaft member second body 62. To connect fluid delivery tubing 26 to barbed connector portion 54, the lumen 27 of fluid delivery tubing 26 may interference (friction or press) fit over the outside diameter of barbed connector portion 54 to provide an interference fit and seal therebetween.

Figure 8:
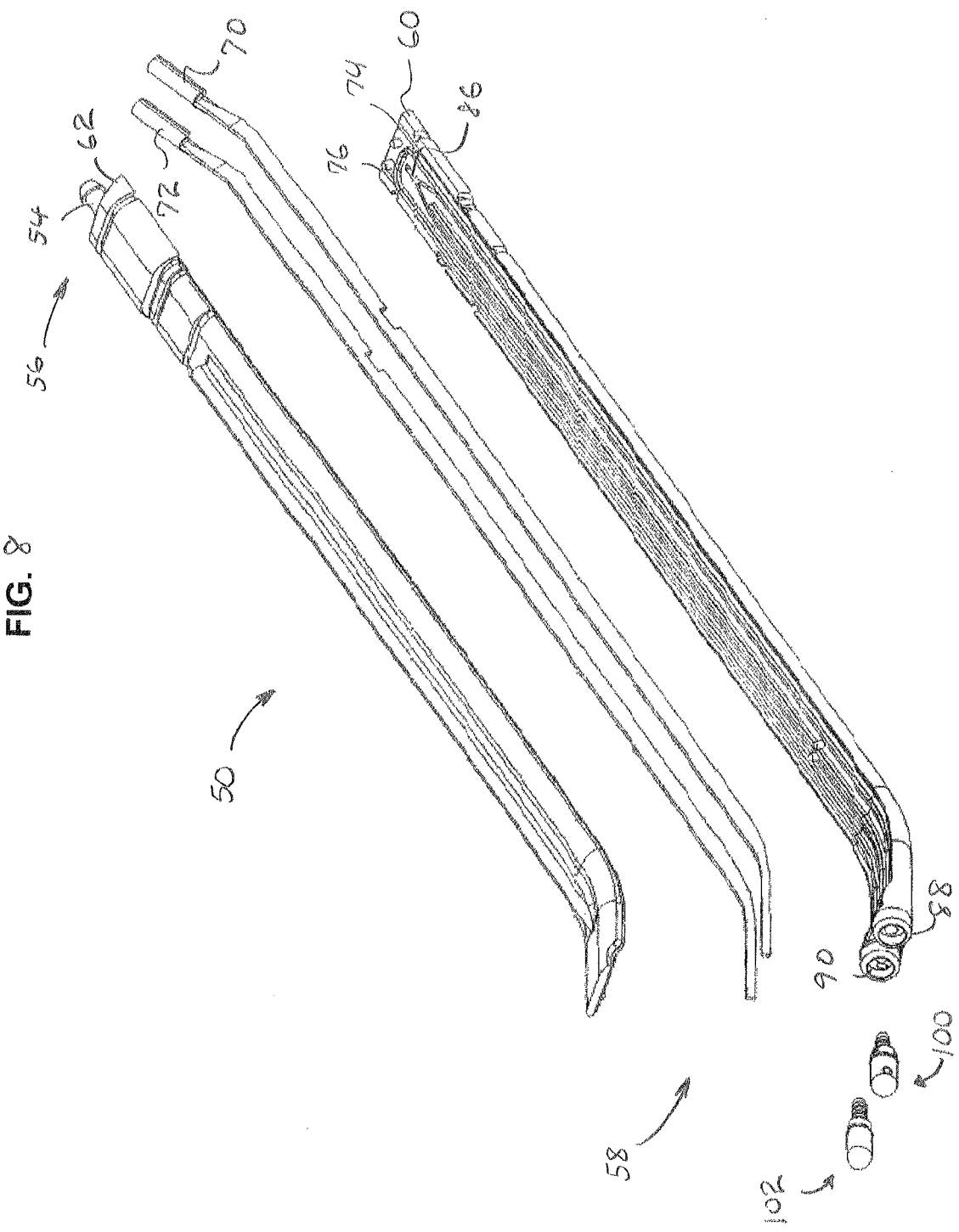
FIG. 8 is an exploded perspective view of the shaft member of FIGS. 6 and 7.
Figure 9:
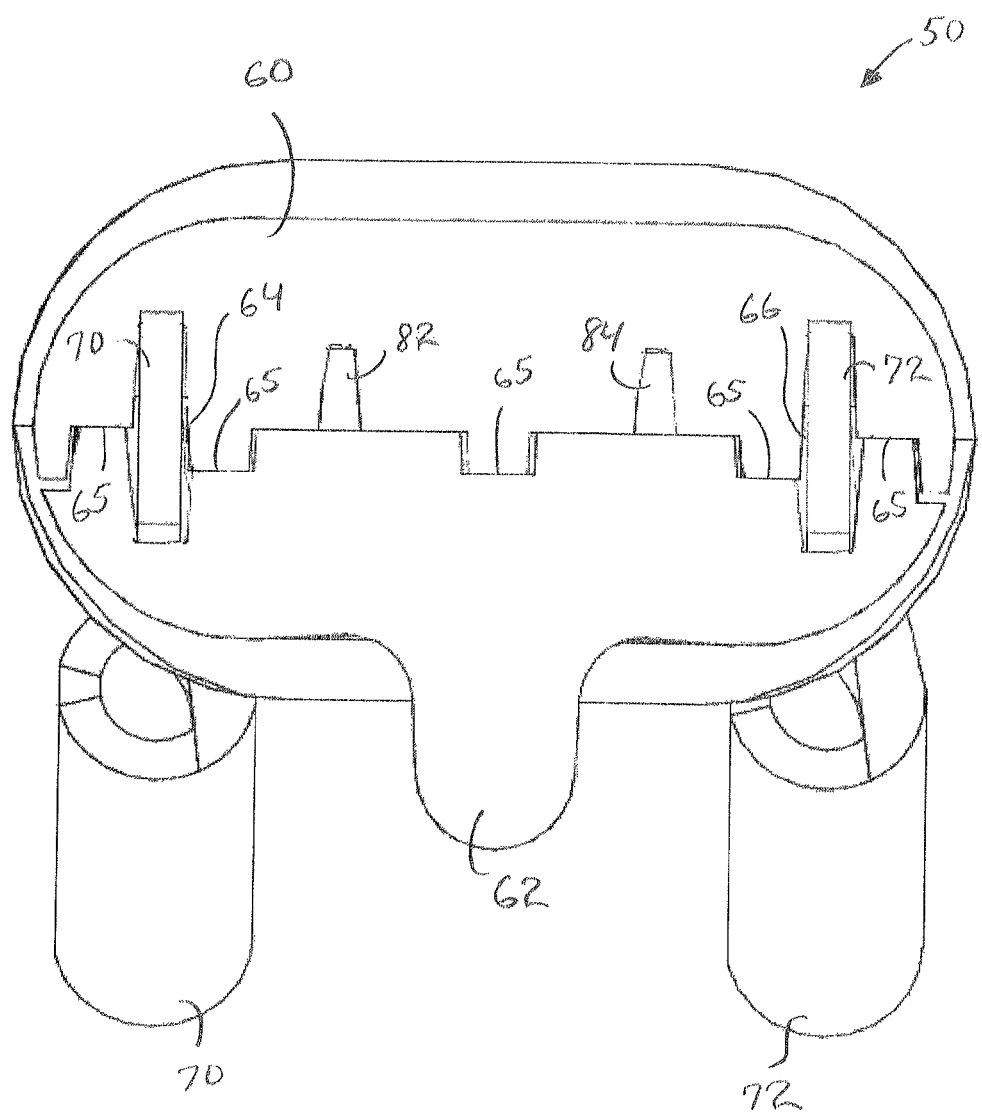
FIG. 9 is a close-up cross-sectional view of the shaft member of FIGS. 6 and 7 taken along line 9-9 of FIG. 6.
Figure 10:
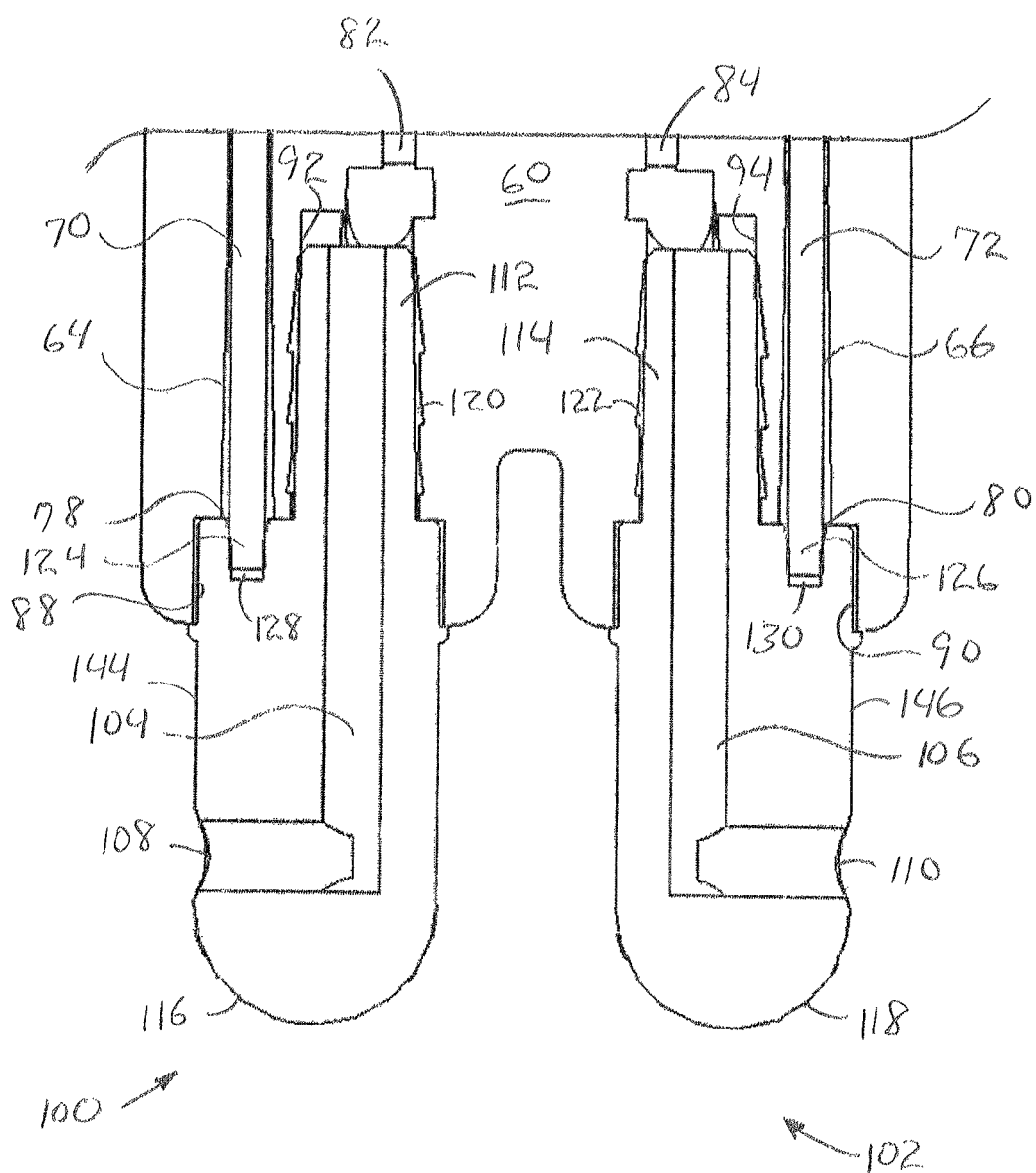
FIG. 10 is a close-up cross-sectional view of the shaft member of FIGS. 6 and 7 taken along line 10-10 of FIG. 6.

As shown in FIGS. 8-10, shaft member first body 60 and shaft member second body 62 comprise two opposing, mating halves of shaft member 50 which may form a clamshell design. Shaft member first body 60 and shaft member second body 62 are joined together along a length of the shaft member 50, from a proximal end 56 to a distal end 58 thereof. Shaft member first body 60 and shaft member second body 62 may particularly be made of a rigid plastic material such as thermoplastic acrylonitrile-butadiene-styrene (ABS) or polycarbonate (PC). As used herein, a rigid plastic may be understood to be a plastic having a modulus of elasticity either in flexure or in tension greater than 700 MPA (100 kpsi) at 23° C. and 50% relative humidity when tested in accordance with ASTM methods D-747, D-790, D-638, or D-882. However, this definition is not necessarily exhaustive, but merely inclusive. Shaft member first body 60 and shaft member second body 62 may be joined by thermoplastic welding, and more particularly ultrasonic welding. In this manner, a hermetic seal may be provided between shaft member first body 60 and shaft member second body 62.

Shaft member 50 includes a plurality of longitudinally oriented, tubular (enclosed), shaft member passages 64, 66, 82 and 84, with each having a length defined by the shaft member first body 60 and the shaft member second body 62. The passages 64, 66, 82 and 84 may be parallel and positioned to a side of one another. As shown, adjacent shaft member passages may be separated from one another by a common weld line or seam 65 which may hermetically seal the passages 64 and 66 from 82 and 84.

Outer (lateral) passages 64, 66 of shaft member 50 more particularly comprise electrical passages which are parallel and isolated from one another, and which contain planar electrical conductors 70, 72. Electrical conductors 70, 72 extend along the complete length of passages 64, 66, and extend from entrance apertures 74, 76, respectively, of passages 64, 66 at a proximal end 56 of shaft member 50, as well as extend from exit apertures 78, 80 of passages 64, 66 at a distal end 58 of shaft member 50. In a particular embodiment, electrical conductors 70, 72 are made of metal, and may more particularly be made of sheet metal. In this manner, conductors are rigid and may contribute to the overall stiffness of shaft member 50.

Also at a proximal end 56 of shaft member 50, electrical conductors 70, 72 are electrically coupled to wire conductors 42 within handle. 40 whereby they may receive RF energy conducted through wire conductors 42 from electrosurgical unit 10. At the distal end 58 of shaft member 50, electrical conductors are electrically coupled (via direct physical contact) to electrodes 100, 102, whereby they may conduct the RF energy from electrosurgical unit 10 to electrodes 100, 102.

As shown, electrodes 100, 102 are seated in distal end electrode receptacles 88, 90 and electrical conductors 70, 72 extend through apertures 78, 80 within the receptacles 88, 90 at the base thereof for the electrical conductors 70, 72 to make contact with electrodes 100, 102.

Figure 11:
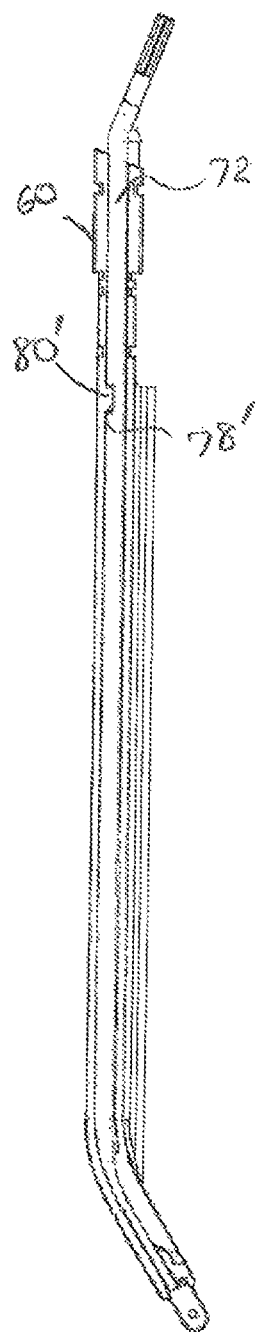
FIG. 11 is a cross-sectional view of the shaft member of FIGS. 6 and 7 taken along a length of conductor 70.

By design, electrical conductors 70, 72 are orientation sensitive and configured to inhibit improper installation within shaft member 50. Furthermore, electrical conductors 70, 72 and at least one of the shaft member first body 60 and a shaft member second body 62 have interconnecting mating features to position each electrical conductor 70, 72 relative, to at least one of the shaft member first body 60 and a shaft member second body 62. As shown in FIG. 11, the interconnecting mating feature of each electrical conductor 70, 72 comprises a keyway 78' and the interconnecting mating feature of at least one of the shaft member first body 60 and shaft member second body 62 comprises a key 80' (shown with shaft member first body 60) configured to interconnect with the keyway. In an alternative embodiment, the keyway may be provided with at least one of the shaft member first body 60 and shaft member second body 62 and the key may be provided with the electrical conductor 70, 72.

Returning to FIGS. 8-10, inner (medial) passages 82, 84 of shaft member 50 more particularly comprise fluid delivery passages. At the proximal end 56 of shaft member 50, passages 82, 84 may branch from a common proximal fluid delivery passage 86 which passes through shaft member barbed connector portion 54 and which is in fluid communication/connected with the lumen 27 of fluid delivery tubing 26.

At the distal end 58 of shaft member 50, passages 82, 84 may be in fluid communication with fluid delivery passages 104, 106 which pass through electrodes 100, 102 and terminate in exit apertures 108, 110. As shown, apertures 108, 110 are at least partially defined by electrodes 100, 102, respectively, and more particularly, are completely defined by electrodes 100, 102, respectively. In the foregoing manner, exit apertures 108, 110 provide fluid outlets or exits configured to provide fluid 22 therefrom directly onto electrodes 100, 102. Furthermore, as shown, exit apertures 108, 110 are proximal to a distal end of electrodes 100, 102, as well as located on lateral portions of electrodes 100, 102.

Thus, during use of device 30a, fluid 22 from fluid source 20 is communicated through a tubular passage provided by lumen 27 of fluid delivery tubing 26, after which it flows through tubular fluid delivery passage 86 and tubular fluid delivery passages 82, 84 of shaft member 50, and then to tubular fluid delivery passages 104, 106 of electrodes 100, 102. After flowing through tubular fluid delivery passages 104, 106 of electrodes 100, 102, fluid 22 may be expelled from fluid outlets 108, 110 onto electrodes 100, 102.

As shown in FIG. 10, a female proximal connector portion 92, 94 of each electrode receptacle 88, 90 may be configured to form an interference (friction or press) fit with a male proximal connector portion 112, 114 of each electrode 100, 102. More particularly, the female connector portion 92, 94 of each electrode receptacle 88, 90 may comprise a cylindrical recess and the male connector portion 112, 114 of each electrode 100, 102 may comprise a barbed connector portion 120, 122 configured to fit within the cylindrical recess. In order to increase the efficiency of the design, the first electrode fluid delivery passage 104 may pass through the first electrode connector portion 112 configured to connect the first electrode 100 to the shaft member 50, and the second electrode fluid delivery passage 106 may pass through the second electrode connector portion 114 configured to connect the second electrode 102 to the shaft member 50.

In the illustrated embodiment, electrodes 100, 102 may be configured to slide across a tissue surface in a presence of the RF energy from electrosurgical unit 10 and fluid 22 from the fluid source 20. As shown, electrodes 100, 102 may be laterally and spatially separated (by empty space), and configured as mirror images in size and shape with a blunt distal end surface 116, 118 devoid of edges (to provide a uniform current density and treat tissue without necessarily cutting). More particularly, each distal end surface 116, 118 of electrodes 100, 102 may comprise a spherical surface, and more particularly comprise a hemispherical surface with an arc of 180 degrees. The spherical surface may be defined by a uniform radius along the arc, which may be in the range between and including 1.25 mm to about 2.5 mm. Electrodes 100, 102 may particularly comprise an electrically conductive metal, such as stainless steel. Other suitable materials may include titanium, gold, silver and platinum.

During manufacture of the device 30a, electrical conductors 70, 72 are first installed and positioned with shaft member first body 60. Thereafter, shaft member first body 60 and shaft member second body 62 may be joined by ultrasonic welding. Thereafter, electrodes 100, 102 way be joined to shaft member 50 by inserting male connector portions 112, 114 of electrodes 100, 102 into female connector portions 92, 94 of electrode receptacles 88, 90 of shaft member 50. Prior to inserting male connector portions 112, 114 of electrodes 100, 102 into female connector portions 92, 94, electrodes 100, 102 may be heated. In this manner, electrodes 100, 102 may heat and soften the female connector portions 92, 94 of electrode receptacles 88, 90 during insertion thereof. In this manner, which may be referred to as heat-staking, the insertion force may be reduced, and the plastic material defining female connector portions 92, 94 may flow to better join/grasp with the barbs and adhesively bond, as well as mechanically bond, to electrodes 100, 102. In this manner a hermetic seal may be provided between electrodes 100, 102 and electrode receptacles 88, 90. Alternatively, electrodes 100, 102 may be ultrasonically welded to electrode receptacles 88, 90 of shaft member 50.

At the same time electrodes 100, 102 are joined to shaft member 50 by inserting male connector portions 112, 114 of electrodes 100, 102 into female connector portions 92, 94 of electrode receptacles 88, 90 of shaft member 50, a distal portion 124, 126 of electrical conductors 70, 72 may be inserted into receptacles 128, 130 of electrodes 100, 102 to establish physical contact therewith for electrical communication.

Figure 12:
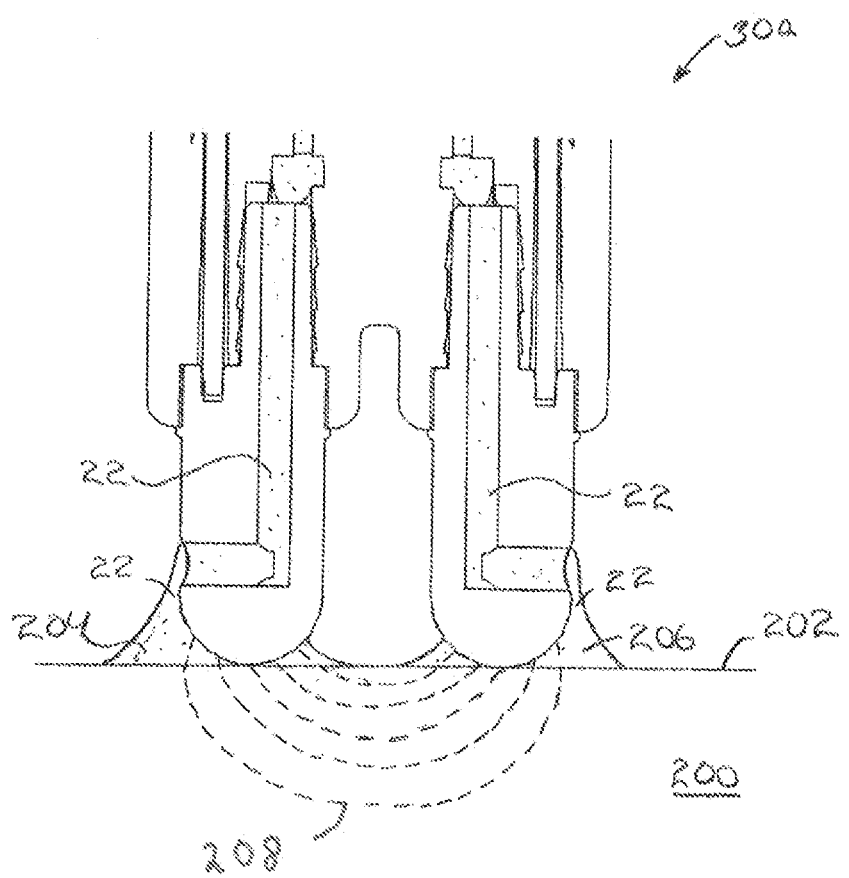
FIG. 12 is a close-up cross-sectional view of a tip portion of the device of FIG. 4 with an exemplary fluid coupling to a tissue surface of tissue.

As shown in FIG. 12, fluid couplings 204, 206 comprise discrete, localized webs and more specifically comprise triangular shaped webs providing fluid 22 between surface 202 of tissue 200 and electrodes 100, 102. When the user of electrosurgical device 30a places electrodes 100, 102 at a tissue treatment site and moves electrodes 100, 102 across the surface 202 of the tissue 200, fluid 22 is expelled from fluid outlet openings 108, 110 around and on surfaces 116, 118 of electrodes 100, 102 and onto the surface 202 of the tissue 200 via couplings 204, 206. At the same time, RF electrical energy, shown by electrical field lines 208, is provided to tissue 200 at tissue surface 202 and below tissue surface 202 into tissue 200 through fluid couplings 204, 206.

Fluid 22, in addition to providing an electrical coupling between the device 30a and tissue 200, lubricates surface 202 of tissue 200 and facilitates the movement of electrodes 100, 102 across surface 202 of tissue 200. During movement of electrodes 100, 102, electrodes 100, 102 typically slide across the surface 202 of tissue 200. Typically the user of device 30a slides electrodes 100, 102 across surface 202 of tissue 200 back and forth with a painting motion while using fluid 22 as, among other things, a lubricating coating. The thickness of the fluid 22 between the distal end surface of electrodes 100, 102 and surface 202 of tissue 200 at the outer edge of couplings 204, 206 may particularly be in the range between and including about 0.05 mm to 1.5 mm. Also, in certain embodiments, the distal end tip of electrodes 100, 102 may contact surface 202 of tissue 200 without any fluid 22 in between.

As shown in FIG. 12, fluid couplings 204, 206 comprise discrete, localized webs and more specifically comprise triangular shaped webs providing fluid 24 between surface 202 of tissue 200 and electrodes 100, 102. When the user of electrosurgical device 30a places electrodes 100, 102 at a tissue treatment site and moves electrodes 100, 102 across the surface 202 of the tissue 200, fluid 22 is expelled from fluid outlet openings 108, 110 around and on surfaces 116, 118 of electrodes 100, 102 and onto the surface 202 of the tissue 200 via couplings 204, 206. At the same time, RF electrical energy, shown by electrical field lines 208, is provided to tissue 200 at tissue surface 202 and below tissue surface 202 into tissue 200 through fluid couplings 204, 206.

In certain surgical procedures, a surgeon working with device 30a may wish to better ensured that the only tissue to be treated is adjacent the distal end surfaces 116, 118 of electrodes 100, 102, and not tissue which may be adjacent the side surfaces 144, 146 of electrodes 100, 102.

Figure 13:
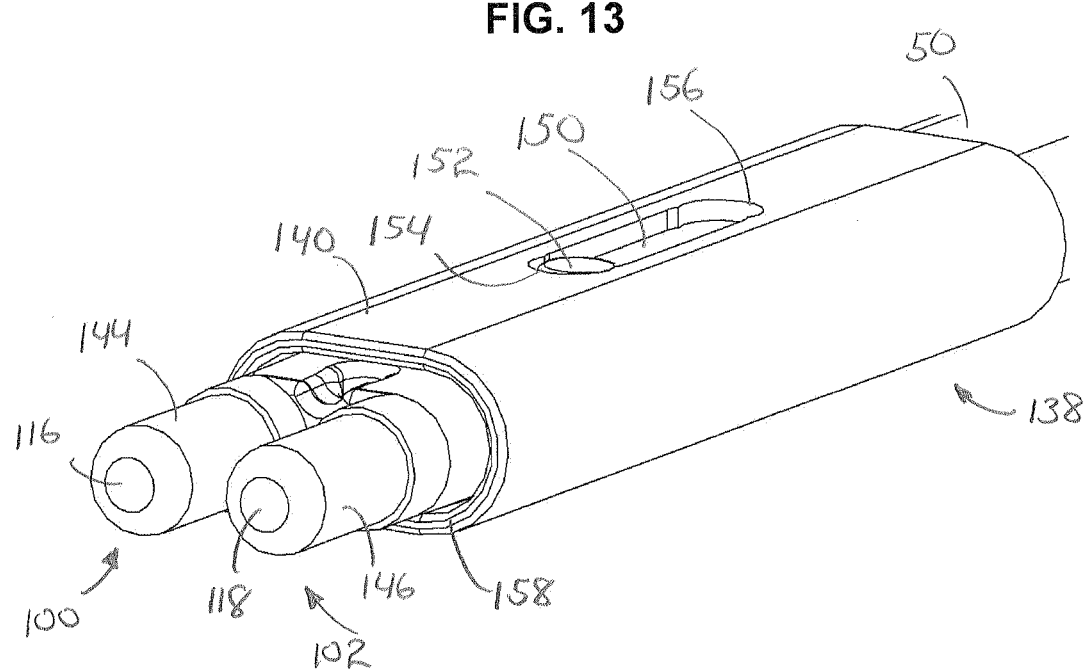
FIG. 13 is a close-up perspective view of the tip portion of the device of FIG. 4 with an electrode sheath in a retracted position.
Figure 14:
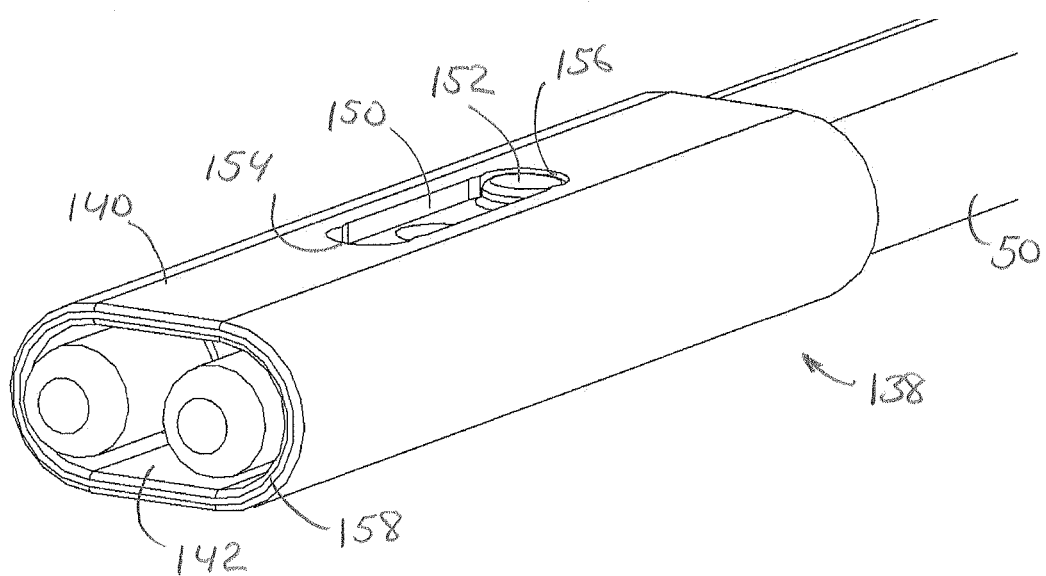
FIG. 14 is a close-up perspective view of the tip portion of the device of FIG. 4 with the electrode sheath in an extended position.

Referring to FIGS. 13 and 14, device 30a may include an electrically insulative movable sheath 138 which may cover at least a portion of electrodes 100, 102. As shown in FIGS. 13 and 14, sheath 138 comprises an oval shaped elongated body 140 with shaft member 50 contained in the tubular passage 142 which extends through body 140, whereby body 140 overlies shaft member 50 and may move (slide) relative to shaft member 50. More particularly, body 140 may extend distally to cover the side surfaces 144, 146 of electrodes 100, 102, and retract proximally to uncover and expose the side surfaces 144, 146 of electrodes 100, 102, while distal end surfaces 116, 118 remain uncovered and exposed to treat tissue. Body 140 may particularly comprise an electrically insulative material, and particularly a thermoplastic polymer material such as polyethylene or polypropylene.

Figure 15:
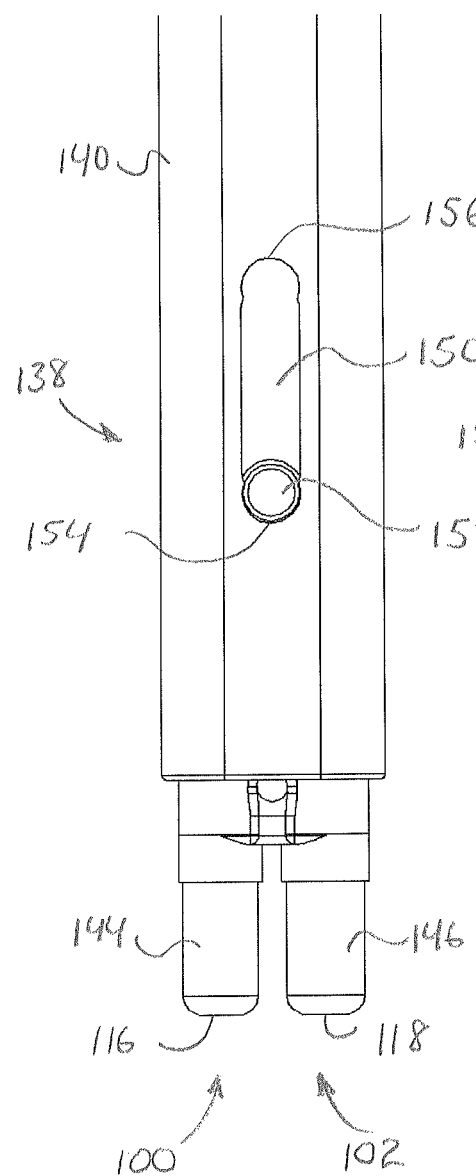
FIG. 15 is a close-up side view of the tip portion of the device of FIG. 4 with an electrode sheath in a retracted position.
Figure 16:
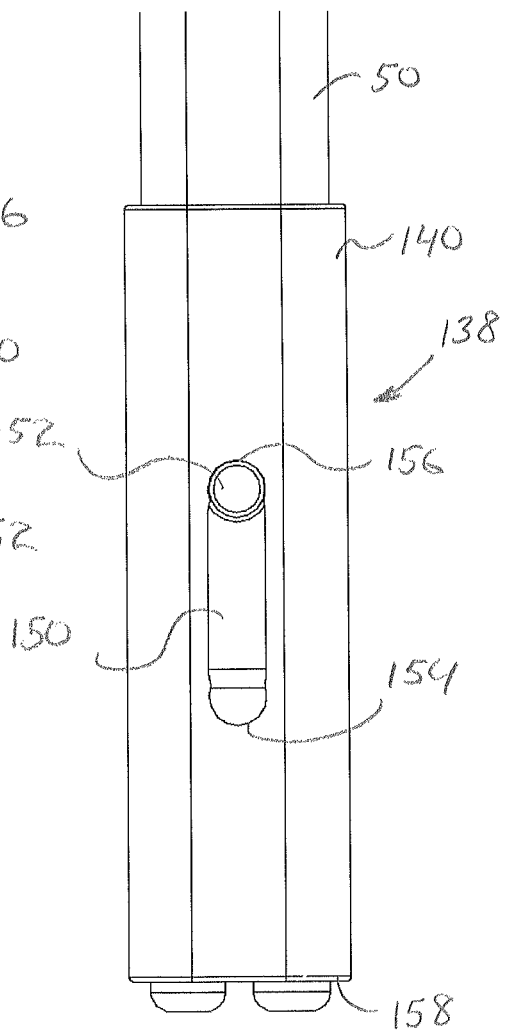
FIG. 16 is a close-up side view of the tip portion of the device of FIG. 4 with the electrode sheath in an extended position.

As best shown in FIGS. 15 and 16, the distal end surfaces 116, 118 of electrodes 100, 102 may be made flat to allow the electrodes 100, 102 to more uniformly compress blood vessels being treated with device 30a as more fully discussed below. Furthermore, sheath 138 may be configured as to cover the side surfaces 144, 146 of electrodes 100, 102 when extended without the distal end 158 of body 140 extending distally past the distal end surfaces 116, 118 of electrodes 100, 102. In this manner, the user of device 30a may be better assured that the electrodes 100, 102 may still contact the tissue when the sheath 138 is extended.

As shown, body 140 may further include an oval aperture or slot 150 which is orientated longitudinally relative to a longitudinal axis of shaft member 50. Within slot 150 may be located a cylindrical pin or other protrusion 152 which protrudes from shaft member 50. In the foregoing manner, as shown in FIGS. 13 and 15, sheath 138 may move proximally until a distal portion 154 of the body 140 defining slot 150 makes contact with protrusion 152. Alternatively, as shown in FIGS. 14 and 16, sheath 138 may move distally until a proximal portion 156 of the body 140 defining slot 150 makes contact with protrusion 152. In the foregoing manner, the sheath 138 is operable with the shaft member 50 to limit distal and proximal movement of the sheath 138, here with the sheath 138 and shaft member 50 having cooperating elements, namely slot 150 and protrusion 152, to limit distal and proximal movement of the sheath 138.

With sheath 138, a surgeon presented with lateral tissue adjacent side surfaces 144, 146 of device 30a, and which is not intended to be treated by electrodes 100, 102, may push the sheath 138 with his/her index finger as to extend the sheath 138 distally. In this manner, the sheath 138 may cover side surfaces 144, 146 of electrodes 100, 102 as to inhibit the side surfaces 144, 146 from treating tissue adjacent thereto. Thereafter, when the surgeon wishes to treat tissue adjacent surfaces 144, 146 of electrodes 100, 102, he/she may pull movable sheath 138, also with his/her index finger, as to retract sheath 138 proximally. In this manner, the sheath 140 may now uncover and expose side surfaces 144, 146 of electrodes 100, 102 as to allow the side surfaces 146, 146 to treat tissue adjacent thereto.

Another embodiment of device 30 is shown in FIGS. 17-21 as device 30b. In contrast to device 30a, shaft member 50 may comprise two adjacent, rigid, self-supporting hollow tubes 160, 162. Tubes 160, 162 may particularly comprise thick walled hypodermic stainless steel tubing, and have sufficient rigidity to maintain their form during use of device 30b without kinking or significant bending. Crimp terminals 48 connect to a proximal portion of tubes 160, 162 to provide electrical coupling therebetween. In order to electrically insulate tubes 160, 162 from one another, the outer surface of tubes 160, 162 may be surrounding by an electrical insulator 164, 166, comprising an electrically insulating material, along their exposed lengths (e.g., the portion outside the confines of the handle 40a, 40b). Insulator 164, 166 preferably comprises a shrink wrap thermoplastic polymer tubing.

With regards to fluid connections and communication, fluid 22 from the fluid source 20 is first communicated through lumen 27 of delivery tubing 26. Delivery tubing 26 particularly feeds into an inlet lumen of a Y-splitter 164 which is in fluid communication with two outlet lumens therein to provide fluid communication to the lumens of delivery tubing 168, 170 to feed each tube 160, 162. The lumens of tubing 168, 170 may be interference fit over the outside diameter of tubes 160, 162 to provide a press fit seal there between. Fluid 22 may then be communicated down lumens of tubes 160, 162 where it is expelled from fluid outlets 108, 110 (see FIG. 10). Electrodes 100, 102 may be particularly assembled adjacent the distal end of tubes 160, 162 via a mechanical press (interference) fit or welding.

Figure 17:
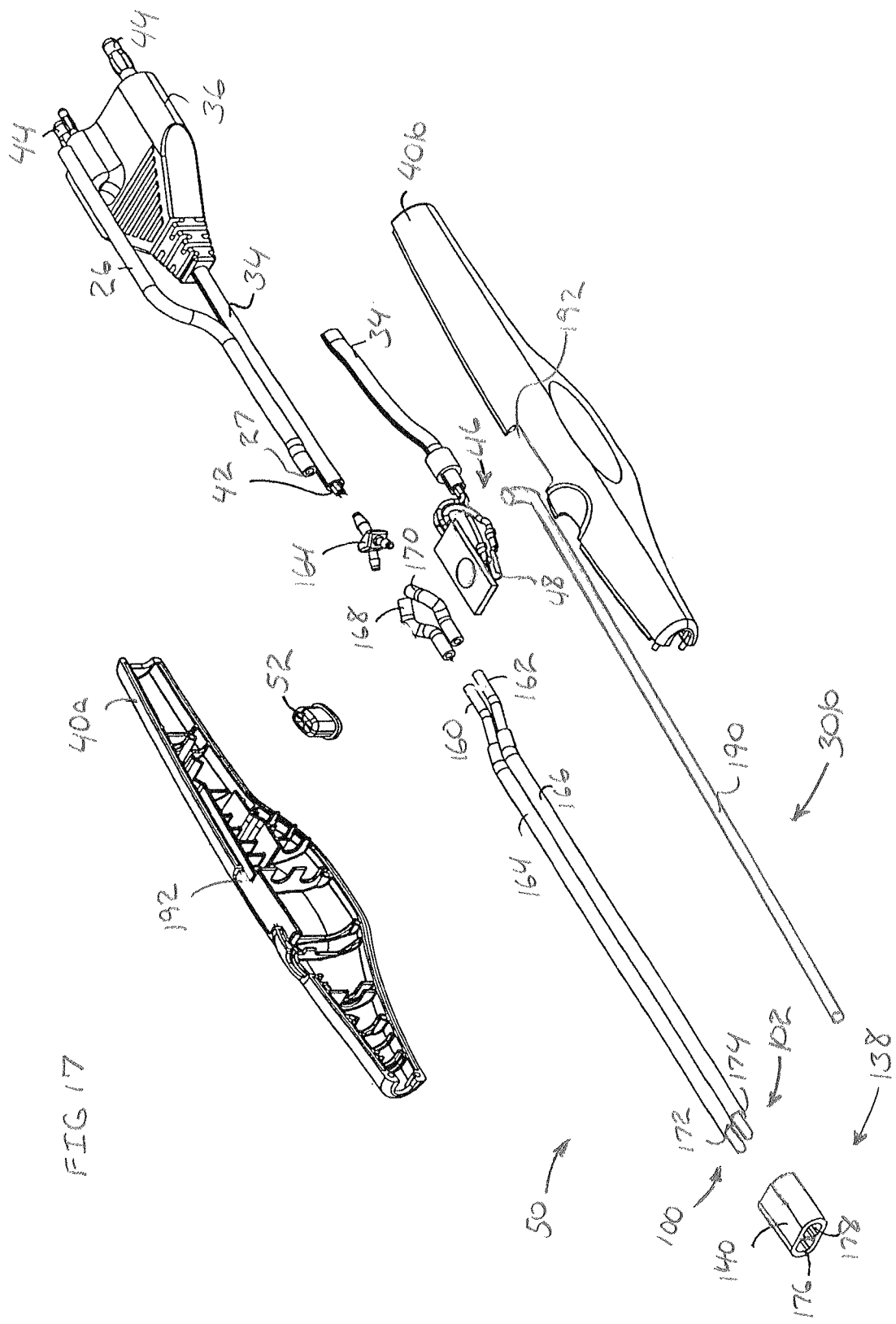
FIG. 17 is an exploded perspective view of another electrosurgical device according to the present invention with another electrode sheath.
Figure 18:
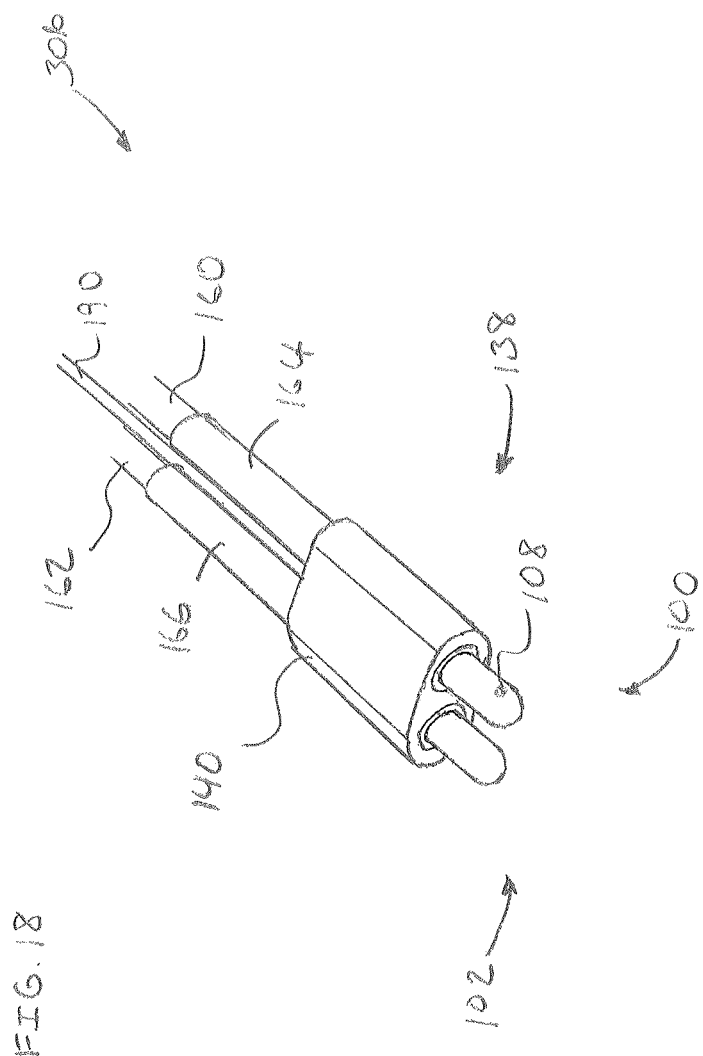
FIG. 18 is a perspective view of the back side of a distal portion of the device of FIG. 15 with the electrode sheath.

Similar to device 30a, device 30b may include an electrically insulative movable sheath 138 which covers at least a portion of electrodes 100, 102. As best shown in FIGS. 17 and 18, sheath 138 comprises a body 140. Each tube 160, 162 of shaft member 50 is contained within a tubular passage 176, 178 which extends through body 140, whereby body 140 overlies shaft member 50 and may move (slide) relative to shaft member 50. Also similar to device 30a, sheath 138 may extend distally to cover the side surfaces 144, 146 of electrodes 100, 102 of device 30b, and may retract proximally to uncover and expose the side surfaces 144, 146 of electrodes 100, 102, while distal end surfaces 116, 118 remain uncovered and exposed to treat tissue.

Sheath 138 of device 30b may be operable with shaft member 50 to increase and decrease a lateral spacing of electrodes 100, 102 relative to each other. Referring to FIGS. 20-21, a proximal portion 177 of tubular passage 178 is parallel to tubular passage 176, while a distal portion 179 of tubular passage 178 is angled (diverges distally and converges proximally) relative to tubular passage 176, which is linear (straight). Consequently, as sheath 138 is moved distally, protrusion 180, which is in the form of a circular ring, and which may be part of either shaft member 50 or electrode 102, will contact surface 182 defining angled portion 179 of tubular passage 178, causing tube 162 and electrode 102 to move towards tube 160 and electrode 100, respectively, to decrease the gap separation GS between electrodes 100, 102 as shown in FIG. 21.

Alternatively, when sheath 138 is moved proximally, protrusion 180 will contact surface 184 defining angled portion 179 of tubular passage 178, causing tube 162 and electrode 102 to move away from tube 160 and electrode 100, respectively, to increase the gap separation GS between electrodes 100, 102 as shown in FIG. 20. In the foregoing manner sheath 138 is movable distally to cover the sides 144, 146 of electrodes 100, 102 and simultaneously decrease the lateral spacing of the electrodes 100, 102 relative to each other, as well as being movable proximally to uncover and expose the sides 144, 146 of electrodes 100, 102 and simultaneously increase the lateral spacing of electrodes 100, 102 relative to each other.

Figure 22:
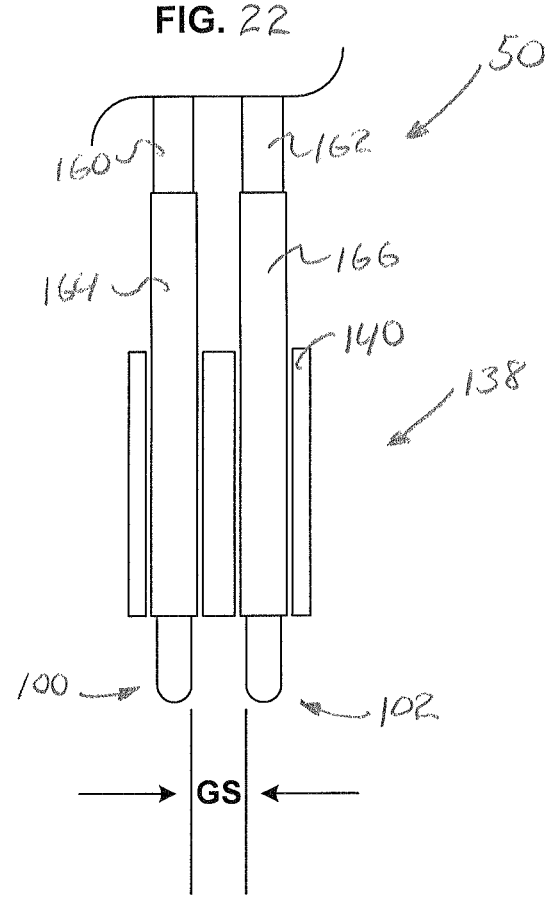
FIG. 22 is a cross-sectional view of another electrode sheath according to the present invention.

In addition to the forgoing, sheath 138 extends between electrodes 100, 102. In this manner, fluid from fluid outlets 108, 110 is inhibited from forming a fluid bridge between electrodes 100, 102, which may result in the fluid creating an electrical shunt therebetween resulting in power loss to treat the tissue. As shown in FIG. 22, sheath 138 may also be configured to maintain a constant separation distance between the electrodes 100, 102, which does not change whether the sheath 138 is extended or retracted.

Returning to FIG. 17, sheath 138 may be operable by use of an actuator mechanism which comprises an elongated member 190 in the form of a push/pull rod which extends from the handle 40 and is connected within a bore 194 (see FIG. 19) at proximal end of body 140 to afford movement of sheath 138. The actuation mechanism, which moves proximally and distally, extends through aperture 192 in handle 40, may be actuated (pushed and pulled) by the index finger of a surgeon using device 30b. This actuation mechanism may be particularly useful when device 30b is used during minimally invasive surgery, such as through a trocar, and the shaft member 50 may be too long for the surgeon to actuate sheath 138 without such.

Figure 23:
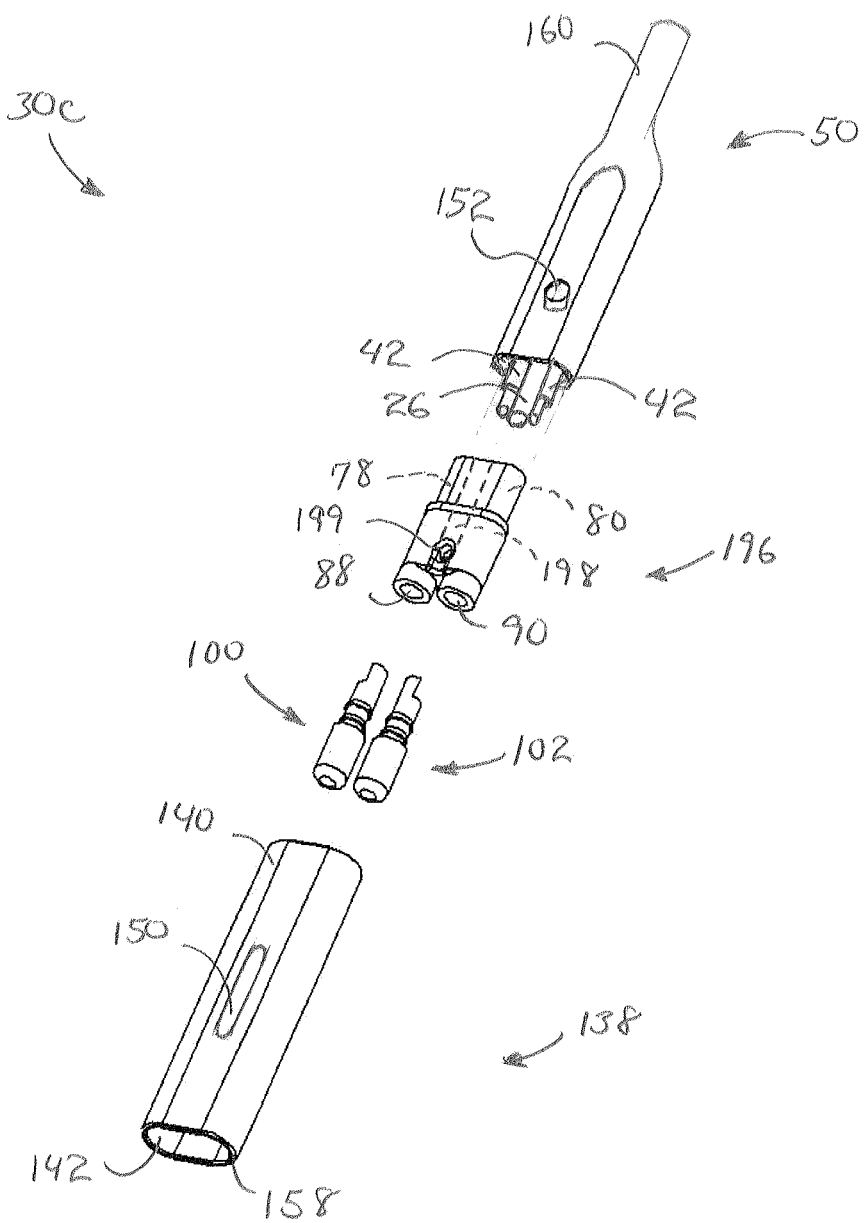
FIG. 23 is an exploded perspective view of another electrosurgical device according to the present invention.

Another embodiment of device 30 is shown in FIG. 23 as device 30c. In contrast to device 30b, shaft member 50 may comprise a single, rigid, self-supporting, hollow tube 160, which may comprise thick walled hypodermic stainless steel tubing, and have sufficient rigidity to maintain its form during use of device 30c without kinking or significant bending. A distal portion of the cylindrical tube 160 may be flattened into the shape of an oval.

At the distal end of tube 160 may be inserted an insulator housing 196 which secures electrodes 100, 102 to device 30a. Housing 196 may particularly include electrode receptacles 88, 90 for electrodes 100, 102. To provide electrical connection to electrodes 100, 102, wire conductors of insulated wires 42 may extend distally down the lumen of the tube 160 and extend into passages 78, 80 of housing 196 to make contact with electrodes 100, 102 within receptacles 88, 90 and connect directly thereto, particularly by welding.

With regards to fluid connections, fluid delivery tubing 26 may also extend distally down the lumen of tube 160 and connect to housing 196. Fluid 12 may then flow through lumen 27 of delivery tubing 26 and into a fluid passage 198 and be expelled from fluid outlet 199.

Turning to sheath 138, sheath 138 has a construction which is similar to that of device 30a. Thus, device 30c provides an alternative device configuration, particularly of shaft member 50, which also may make use of sheath 138.

The bipolar devices disclosed herein may be particularly useful as non-coaptive tissue sealers in providing hemostasis during surgery. In other words, grasping of the tissue is not necessary to shrink, coagulate and seal tissue against blood loss, for example, by shrinking collagen and associated lumens of blood vessels (e.g., arteries, veins), thereby inhibiting blood flow therethrough and therefrom, to provided the desired hemostasis of the tissue. More particularly, the devices may be useful to shrink blood vessels, either severed or unsevered, during spine surgery, such as blood vessels of the vertebral venous and/or arterial systems during, for example, a discectomy.

Intervertebral discs are flexible pads of fibrocartilaginous tissue tightly fixed between the vertebrae of the spine. The discs comprise a flat, circular capsule roughly an inch in diameter and about 0.25 inch thick, made of a tough, fibrous outer membrane called the annulus fibrosus, surrounding an elastic core called the nucleus pulposus.

Under stress, it is possible for the nucleus pulposus to swell and herniate, pushing through a weak spot in the annulus fibrosus membrane of the disc and into the spinal canal. Consequently, all or part of the nucleus pulposus material may protrude through the weak spot, causing pressure against surrounding nerves which results in pain and immobility.

Where a damaged intervertebral disc must be removed from the patient as part of a discectomy and a subsequent fusion of vertebral bodies of the superior and inferior vertebrae, the surgeon may first retract soft tissue from the point of entry to the vertebrae to be fused. Around and attached to the vertebrae are, among other things, various muscles which act on the vertebrae to affect movement of the upper body. As the muscle and other soft tissue are retracted, the bipolar devices disclosed herein may be used to treat the retracted tissue, as well as the surfaces of tissue to any cavity (e.g. pocket or crevice) created on approach to the disc. At this time, the devices disclosed herein may generally be used with the sheath retracted, to expose the side surfaces of the electrodes to treat the tissue on the side surfaces of the cavity.

Once the retraction is complete, and the disc is exposed, it may be removed. The vertebrae may then be aligned to straighten the spinal column, and stabilized relative to one another by rods or other supports which are attached to the vertebrae by numerous fastening techniques. The surgeon may then place bone graphs across the exposed surfaces of adjoining vertebrae and restore the location of the soft tissue to cover the bone graphs and vertebrae. The graphs regenerate, grow into bone and fuse the vertebrae together, with the rod functioning as a temporary splint which stabilizes the spinal column while the bone fuses together over a period of months.

During the discectomy and fusion, the bipolar devices of the present invention may be particularly useful to shrink and seal blood vessels of the vertebral venous and/or arterial systems. However, certain of these blood vessels may be adjacent nerves which are not intended to be treated by the bipolar devices. Consequently, in this situation the sheath may be extended to cover the side surfaces of the electrodes and inhibit undesirable treatment of adjacent nerves. Furthermore, the base of the cavity may be particularly narrow, and extending the sheath may decrease the footprint of the electrodes to better provide access to a narrow tissue treatment site.

The vertebral venous system includes any of four interconnected venous networks surrounding the vertebral column. These are known as the anterior external vertebral venous plexus (the system around the vertebral bodies), the posterior external vertebral venous plexus (the system around the vertebral processes), the anterior internal vertebral (epidural) venous plexus (the system running the length of the vertebral canal anterior to the dura) and the posterior internal vertebral (epidural) venous plexus (the system running the length of the vertebral canal posterior to the dura), with the latter two constituting the epidural venous plexus. The veins of the exterior vertebral venous plexus communicate with the veins of the interior vertebral venous plexus through intervertebral veins and anterior and posterior segmental medullary/radicular veins of each vertebral level.

The vertebral arterial system includes the segmental arteries of the vertebral column which supply anterior and posterior radicular arteries of the various vertebral levels. In thoracic and lumbar regions, segmental arteries include the posterior intercostal, subcostal and lumbar arteries, which arise from posterior aspect of the aorta. The blood supply to the spinal column is derived from the segmental arteries, which supply two networks: one feeds the bony elements of the vertebrae, the paraspinal muscles, and the extradural space; and the other, an inner network, nourishes the spinal cord itself.

Extending from the aorta, the segmental arteries hug the perimeter of the vertebral bodies of the vertebrae, giving off paravertebral anastomoses, prevertebral anastomoses and a main dorsal branch as they approach the neural foramina. This main dorsal branch continues posteriorly below the transverse process of the vertebrae, supplying the bone of the posterior elements of the vertebrae and the paraspinal muscles. Shortly after its origin, the dorsal branch gives off a spinal branch, which supplies the anterior radicular artery and anterior segmental medullary artery, which ultimately supplies the anterior spinal artery. The spinal branch also supplies a branch to the vertebral body and dura mater, and the posterior radicular artery which ultimately supplies the posterior spinal arteries.

During a posterior discectomy, the devices of the present invention may be particularly used by a surgeon to seal veins of the posterior external vertebral venous plexus, posterior internal vertebral (epidural) venous plexus and anterior internal vertebral (epidural) venous plexus prior to entering the intervertebral disc space. Alternatively, during an anterior discectomy, the devices of the present invention may be particularly used by a surgeon to seal veins of the anterior external vertebral venous plexus and segmental arteries, particularly the anterior and lateral-anterior portions adjacent the vertebral bodies.

During a discectomy blood vessels are often cut, ruptured or otherwise severed. These blood vessels bleed, and the resulting blood can flow into the tissue treatment site making visibility more difficult and prolonging the procedure. A method of the present invention may be used to seal such vertebral blood vessels against blood loss before the vessels are cut, rupture or are otherwise severed. This method involves pressing a portion of the blood vessel against a supporting spine structure with the bipolar devices of the present invention, particularly the distal ends 116, 118 of the electrodes 100, 102, to provide a compressed portion of the blood vessel, and heating the compressed portion of the blood vessel with the bipolar device sufficiently to occlude the blood vessel (e.g. by shrinking the vessel and the lumen by shrinkage of the collagen in the vessel and/or welding the opposite internal surfaces of the lumen together by collagen welding) to inhibit a blood flow through the vessel after the bipolar device is removed from the blood vessel.

The supporting spine structure against which the blood vessel is compressed may comprise one or more vertebra of the spine, and may further comprise the vertebral body of the vertebra. The vertebra may comprise one of the cervical vertebrae, thoracic vertebrae, or lumbar vertebrae. In addition to the vertebrae, the support structure may also comprise a spinal ligament, such as the anterior longitudinal ligament or the posterior longitudinal ligament, or an intervertebral disc.

Depending on the type of procedure, the supporting spine structure may further comprise an anterior side of the vertebral body of the vertebra or a lateral-anterior side of the vertebral body of the vertebra, which would be encountered during an anterior approach. For a posterior approach, the supporting spine structure may further comprise a posterior side of the vertebral body of the vertebra or a lateral-posterior side of the vertebral body of the vertebrae. The anterior or posterior approach may be part of an endoscopic spine surgery, laparoscopic spine surgery or open spine surgery.

Due to the rigidity of the vertebra and stability of the vertebrae, the blood vessel may be pressed against the vertebra without the vertebra deforming. In this manner, the blood vessel may be compressed, at which time the compressed portion of the vessel may be heated sufficiently to occlude the blood vessel after the bipolar device is removed from the blood vessel.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes to the extent they are consistent.

What is claimed:

1. An electrosurgical device comprising:
a handle;
a shaft member distal to the handle and having a distal end;
a first elongate electrode having a side surface extending longitudinally along an axis to a first distal end, the first electrode having a first electrode tip surface adjacent to the first distal end, the first electrode tip surface being substantially flat;
a second elongate electrode having a side surface extending longitudinally along the axis to a second distal end, the second electrode having a second electrode tip surface adjacent to the second distal end, the second electrode tip surface being substantially flat;
the first and second electrodes being capable of treating tissue proximate the side surfaces, and distal to the distal end of the shaft member,
the first electrode tip surface laterally spaced from the second electrode tip surface;
an electrode sheath having a distal end, the electrode sheath being movable between an extended position which covers the side surfaces of the first and second electrodes and blocks tissue from coming near the side surfaces of the first and second electrodes but affords contact between the first and second electrode tip surfaces and tissue, and a retracted position that uncovers at least a portion of the elongated electrodes to allow tissue to come near the side surfaces of the first and second electrodes and be treated by the side surfaces of the first and second electrodes; and wherein when the electrode sheath is in the extended position, the first and second electrode tips project beyond the distal end of the electrode sheath.

2. The device of claim 1 wherein:
the sheath is movable distally to cover the sides of the electrode tips; and
the sheath is movable proximally to uncover the sides of the electrode tips.

3. The device of claim 1 wherein:
the sheath overlies the shaft member.

4. The device of claim 1 wherein:
the sheath includes a tubular passage.

5. The device of claim 4 wherein:
the shaft member is within the tubular passage of the sheath.

6. The device of claim 1 wherein:
the sheath is operable with the shaft member to limit distal and proximal movement of the sheath.

7. The device of claim 6 wherein:
the sheath and shaft member having cooperating elements which limit the distal and proximal movement of the sheath.

8. The device of claim 7 wherein:
the cooperating elements comprise a protrusion located on the shaft member and a slot located on the sheath which contains the protrusion.

9. The device of claim 1 wherein:
the sheath is operable with the shaft member to increase and decrease a lateral spacing of the electrode tip surfaces relative to each other.

10. The device of claim 9 wherein:
the sheath is movable distally to cover the sides of the electrode tip surfaces and decrease the lateral spacing of the electrode tip surfaces relative to each other; and
the sheath is movable proximally to uncover the side of the electrode tip surfaces and increase the lateral spacing of the electrode tip surfaces relative to each other.

11. The device of claim 9 wherein:
the sheath is operable with the shaft member to increase and decrease a lateral spacing of the electrode tip surfaces relative to each other by moving at least one of the electrode tip surfaces.

12. The device of claim 9 wherein:
the sheath is operable with the shaft member to increase and decrease a lateral spacing of the electrode tip surfaces relative to each other by moving a portion of the shaft member.

13. The device of claim 1 wherein:
the sheath is operable with at least one of the electrode tip surfaces to increase and decrease a lateral spacing of the electrode tips relative to each other by moving at least one of the electrode tips.

14. The device of claim 1 wherein:
the sheath comprises a first tubular passage and a second tubular passage.

15. The device of claim 14 wherein:
a distal portion of the second tubular passage is angled relative to a distal portion of the first tubular passage.

16. The device of claim 1 further comprising:
a sheath actuation mechanism which extends from the handle and connects to the sheath to activate movement of the sheath from the handle.

17. The device of claim 16 wherein:
the sheath actuation mechanism comprises an elongated member which pushes the sheath distally and pulls the sheath proximally.

18. An electrosurgical device comprising
a handle;
a shaft member distal to the handle;
a first electrode tip and a second electrode tip distal a distal end of the shaft member,
the first electrode tip laterally spaced from the second electrode tip;
an electrode sheath movable to cover and uncover a side of the electrode tips while a distal end of the electrode tips is uncovered to treat tissue;
wherein: the sheath is operable with the shaft member to increase and decrease a lateral spacing of the electrode tips relative to each other;
the sheath comprises a first tubular passage and a second tubular passage;
a distal portion of the second tubular passage is angled relative to the first tubular passage; and the sheath is operable with the shaft member to increase and decrease a lateral spacing of the electrode tips relative to each other by contacting a surface of the sheath defining the angled portion of the second tubular passage with a portion of the shaft member located therein as the sheath is moved proximally and distally, respectfully.

19. An electrosurgical device comprising
a handle;
a shaft member distal to the handle;
a first electrode tip and a second electrode tip distal a distal end of the shaft member,
the first electrode tip laterally spaced from the second electrode tip;
an electrode sheath movable to cover and uncover a side of the electrode tips while a distal end of the electrode tips is uncovered to treat tissue;
the sheath is operable with at least one of the electrode tips to increase and decrease a lateral spacing of the electrode tips relative to each other;
wherein:
the sheath comprises a first tubular passage and a second tubular passage;
a distal portion of the second tubular passage is angled relative to the first tubular passage; and
the sheath is operable with at least one of the electrode tips to increase and decrease a lateral spacing of the electrode tips relative to each other by contacting a surface of the sheath defining the angled portion of the second tubular passage with a portion of one of the electrode tips located therein as the sheath is moved proximally and distally, respectfully.

20. An electrosurgical device comprising:
a handle;
a shaft member distal to the handle and having a distal end;
a first elongate electrode having a side surface extending longitudinally along an axis to a first distal end, the first electrode having a first electrode tip surface adjacent to the first distal end, the first electrode tip surface being disposed substantially orthogonally to the side surface of the first electrode;
a second elongate electrode having a side surface extending longitudinally along the axis to a second distal end, the second electrode having a second electrode tip surface adjacent to the second distal end, the second electrode tip surface being disposed substantially orthogonally to the side surface of the second electrode;

the first and second electrodes being capable of treating tissue proximate the side surfaces, and distal to the distal end of the shaft member, the first electrode tip surface laterally spaced from the second electrode tip surface;

an electrode sheath having a distal end, the electrode sheath being movable between an extended position which covers the side surfaces of the first and second electrodes and blocks tissue from coming near the side surfaces of the first and second electrodes but affords contact between the first and second electrode tip surfaces and tissue, and a retracted position that uncovers at least a portion of the elongated electrodes to allow tissue to come near the side surfaces of the first and second electrodes and be treated by the side surfaces of the first and second electrodes; and wherein when the electrode sheath is in the extended position, the first and second electrode tips project beyond the distal end of the electrode sheath.

* * * * *